(12) United States Patent
Takakura et al.

(10) Patent No.: US 9,034,590 B2
(45) Date of Patent: May 19, 2015

(54) METHOD FOR DETECTING SUBSTANCE IN BIOLOGICAL SAMPLE

(75) Inventors: Yoshimitsu Takakura, Iwata (JP); Naomi Oka, Iwata (JP); Kazuhiro Kondo, Tokyo (JP)

(73) Assignees: JAPAN TOBACCO INC., Tokyo (JP); VIRUS IKAGAKU KENKYUSHO INC., Osaka (JP)

( * ) Notice: Subject to any disclaimer, the term of this patent is extended or adjusted under 35 U.S.C. 154(b) by 374 days.

(21) Appl. No.: 13/258,247

(22) PCT Filed: Mar. 31, 2010

(86) PCT No.: PCT/JP2010/055887
§ 371 (c)(1),
(2), (4) Date: Sep. 21, 2011

(87) PCT Pub. No.: WO2010/114031
PCT Pub. Date: Oct. 7, 2010

(65) Prior Publication Data
US 2012/0088313 A1    Apr. 12, 2012

(30) Foreign Application Priority Data

Mar. 31, 2009 (JP) ................................. 2009-087839

(51) Int. Cl.
| | | |
|---|---|---|
| *G01N 33/543* | (2006.01) | |
| *G01N 33/569* | (2006.01) | |
| *G01N 33/68* | (2006.01) | |

(52) U.S. Cl.
CPC .... *G01N 33/54393* (2013.01); *G01N 33/54306* (2013.01); *G01N 33/54353* (2013.01); *G01N 33/56994* (2013.01); *G01N 33/6854* (2013.01); *G01N 2333/035* (2013.01); *G01N 2333/36* (2013.01)

(58) Field of Classification Search
USPC ......... 436/507, 512, 518, 524, 528, 174, 175, 436/177; 435/5, 6, 7.1, 7.2, 7.5, 7.94, 173.5
See application file for complete search history.

(56) References Cited

U.S. PATENT DOCUMENTS

| 8,343,727 B2 * | 1/2013 | Takakura et al. .............. 435/7.1 |
| 2002/0052009 A1 | 5/2002 | Hornauer et al. |
| 2005/0089983 A1 | 4/2005 | Takakura |
| 2008/0176340 A1 * | 7/2008 | Soldo et al. .................. 436/518 |

FOREIGN PATENT DOCUMENTS

| EP | 2 405 268 A1 | 1/2012 | |
| EP | 2 416 159 A1 | 2/2012 | |
| EP | 2 447 364 A1 | 5/2012 | |
| GB | 2 324 601 A | 10/1998 | |
| JP | 59-99257 A | 6/1984 | |
| JP | 4-236353 A | 8/1992 | |
| JP | 8-043392 * | 2/1996 | ........... G01N 33/543 |
| JP | 8-43392 A | 2/1996 | |
| JP | 8-114590 A | 5/1996 | |
| JP | 2002-48794 A | 2/2002 | |
| JP | 2004-301646 A | 10/2004 | |
| WO | WO 2010/101157 A1 | 9/2010 | |
| WO | WO 2010/114029 A1 | 10/2010 | |
| WO | WO 2010/150375 A1 | 12/2010 | |

OTHER PUBLICATIONS

Extended European Search Report, dated May 3, 2012, for European Application No. 10758802.2.
Green, "Avidin and Streptavidin", Methods in Enzymology, 1990, vol. 184, pp. 51-67.
Green, "Avidin", Adv. Protein Chem., 1975, vol. 29, pp. 85-133.
International Search Report, dated Jun. 29, 2010, for International Application No. PCT/JP2010/055887, with a partial English translation.
Takakura et al., "Tamavidins —novel avidin-like biotin-binding proteins from the Tamogitake mushroom", FEBS Journal, 2009, vol. 276, pp. 1383-1397.
Diamandis et al., "The Biotin-(Strept)Avidin System: Principles and Applications in Biotechnology", Clin. Chem., vol. 37, No. 5 (1991) pp. 625-636.

* cited by examiner

*Primary Examiner* — Gail R Gabel
(74) *Attorney, Agent, or Firm* — Birch, Stewart, Kolasch & Birch, LLP

(57) ABSTRACT

The present invention provides a method for detecting a substance in a biological sample, a carrier for using in the method, and a kit. The method of the present invention includes 1) providing a carrier on which a biotin-binding protein is bound and providing a biotinylated protein by biotinylating a protein that specifically binds to a substance to be detected; 2) binding the biotinylated protein to the carrier provided in step 1) to produce a biotinylated protein-bound carrier; 3) mixing (a) a biological sample, and (b-i) a cell homogenate extract prepared from cells of the same species as that of the host cells used for expressing, for example, the biotin-binding protein in step 1), and a biotin-binding protein, or (b-ii) a cell homogenate extract prepared from cells of the same species as that of the host cells used for expressing, for example, the biotin-binding protein in step 1) and genetically engineered to express a biotin-binding protein, and adding the mixture to the biotinylated protein-bound carrier produced in step 2); and 4) detecting the substance specifically bound to the biotinylated protein.

5 Claims, 2 Drawing Sheets

METHOD FOR DETECTING SUBSTANCE IN BIOLOGICAL SAMPLE

TECHNICAL FIELD

The present invention relates to a method for qualitatively and/or quantitatively detecting a substance in a biological sample. In particular, the method of the present invention can detect even a trace amount of substance that is present in a biological sample and that cannot be readily detected in usual manner.

BACKGROUND ART

In order to detect a substance in a biological sample, a method utilizing a substance that specifically binds to the former substance (substance to be detected) has been widely used. For example, immunoassays utilizing antigen-antibody reactions and nucleic acid hybridization assays utilizing hydrogen bonds between nucleic acid chains are known. For example, in the immunoassay, an antigen, when the substance to be detected is an antibody, or in contrast, an antibody, when the substance to be detected is an antigen, is immobilized on a carrier such as a microplate, microbeads, or a sensor chip, and after the reaction with the substance to be detected, the presence or absence or the degree of the antigen-antibody reaction is measured.

As general means for the immobilization, for example, hydrophobic bonding and covalent bonding are known. In the "hydrophobic bonding", a carrier and a protein that specifically binds to a substance to be detected (hereinafter, may be referred to as "specific protein") are bound to each other by interaction between the hydrophobic surface of the carrier and the hydrophobic moiety of the specific protein. This is convenient from the point of not needing specific reagents. However, such binding is usually weak. In the case where the hydrophobic bonding is applied to, for example, enzyme-linked immunosorbent assay (ELISA), the protein is detached from the carrier during, for example, a washing procedure after binding in many cases. Furthermore, in the case where a specific protein is bound to a carrier by hydrophobic bonding, the function of the protein may be lost completely or partially in many cases. The "covalent bonding" utilizes interaction between functional groups (e.g., amino groups) of a specific protein and functional groups (e.g., carboxyl groups) provided on the surface of the carrier, and is strong. However, after a specific protein is bound to a carrier by covalent bonding, the function of the protein is lost completely or partially in many cases, like the hydrophobic bonding.

In addition to the hydrophobic bonding and the covalent bonding, known is a method for fusing a plurality of histidine molecules to terminals of protein molecules and binding the fusion protein having the histidine tags to, for example, a basal plate, such as a protein chip, having a surface provided with nickel. The interaction between the histidine tags and nickel ions is, however, not very strong, and nickel ions are known to non-specifically bind to a variety of biological molecules.

Alternatively, a method of binding a protein to a carrier using the binding ability of avidin or streptavidin to biotin (vitamin H) has been developed. Avidin is a glycoprotein derived from albumen and extremely strongly binds to biotin. The interaction between avidin and biotin is one of the strongest non-covalent bonds (Green, (1975), Adv Protein Chem, 29: 85-133). Meanwhile, streptavidin is an avidin-like protein derived from actinomycetes and also strongly binds to biotin. Biotin is a molecule having a low molecular weight of 244 and can be easily bound to various biological molecules, such as proteins, nucleic acids, lipids, or sugar chains, using, for example, commercially available kits and also hardly affects the properties of biotinylated molecules. The interaction of (strept)avidin-biotin, because of its high binding force, has been widely used, for example, for detection of antigens and antibodies in the fields of molecular biology and biochemistry (Green, (1990), Methods Enzymol, 184: 51-67). In the case of binding a protein to a carrier using avidin or (strept)avidin, (strept)avidin is immobilized to a basal plate such as a microplate through covalent bonding or hydrophobic bonding, and then a biotinylated protein is bound thereto. Furthermore, a technique of immobilizing basal plate-biotin-avidin-biotin-desired protein in this order is also reported, in which avidin is bound to a basal plate provided with biotin by avidin-biotin binding, and then a biotinylated desired protein is bound to another biotin pocket of the avidin (JP No. H4-236353 A (1992)). A subject substance can be detected using a plate on which a specific protein is immobilized by such a technique.

In such a specific binding assay system using a solid phase on which a protein that specifically binds to a substance, such as an antigen or antibody, to be detected is bound by hydrophobic bonding or covalent bonding, non-specific binding, which causes a background signal and thus should be reduced, is generally a severe problem. In order to solve this problem, the following methods have been proposed for example: a method of adding an extract of a bacterium component to a reagent for detection (JP No. S59-99257 A (1984)); a method of adding a culture component of host cells containing a vector of the same species as that used in production of a recombinant protein capable of specifically binding to a substance to be detected and the vector not containing the gene encoding the protein to a sample (JP No. H8-43392 A (1996)); and a method of heat-treating an aqueous extract from cells of the same species as that producing a recombinant protein capable of specifically binding to a substance to be detected, and the cell not containing this protein, and then adding water-soluble fraction of the heated aqueous extract to a sample (JP No. 2004-301646 A). These methods show some effects on inhibition of non-specific binding.

The assay utilizing the avidin-biotin binding has also a big problem with background signals, like the assay using a solid phase on which a protein that specifically binds to a substance to be detected is bound by, for example, hydrophobic bonding or covalent bonding. Countermeasures have been proposed for solving this problem are, for example: a method in which a sample is put into contact with a solid phase to which inactivated (strept)avidin is bound and then contact with a solid phase to which active (strept)avidin is bound (JP No. H8-114590 A (1996)); a method in which a biotinylated substance is bound to an avidin-bound solid phase, and then this is put into contact with a conjugate of polyethylene glycol and biotin (JP No. H11-211727 A (1999)); and a method in which a biotin-containing solution is put into contact with a solid phase (JP No. 2002-48794 A), in addition to the above-mentioned methods for preventing non-specific binding. Unfortunately, all the methods exhibit insufficient practical advantages.

CITATION LIST

Patent Literature

Patent Literature 1: JP No. S59-99257 A (1984)
Patent Literature 2: JP No. H8-43392 A (1996)

Patent Literature 3: JP No. 2004-301646 A
Patent Literature 4: JP No. H4-236353 A (1992)
Patent Literature 5: JP No. H8-114590 A (1996)
Patent Literature 6: JP No. H11-211727 A (1999)
Patent Literature 7: JP No. 2002-48794 A Non-Patent Literature Non-Patent Literature 1: Green, (1975), Adv Protein Chem, 29: 85-133
Non-Patent Literature 2: Green, (1990), Methods Enzymol, 184: 51-67

SUMMARY OF INVENTION

Technical Problem

It is an object of the present invention to provide a method for qualitatively and/or quantitatively detecting a substance in a biological sample.

Specifically, it is an object of the present invention to provide a method for qualitatively and/or quantitatively detecting or measuring a trace amount of substance that is present in a biological sample while reducing the background signal level.

Solution to Problem

The inventors have diligently studied and, as a result, have arrived at the present invention through a measure for reducing the background signal level, in particular, in order to detect a trace amount of substance that is present in a biological sample, in a system in which a biotinylated protein, the biotinylated protein being a protein that specifically binds to a substance to be detected and has been biotinylated, is immobilized on a carrier through binding between biotin and a biotin-binding protein. Specifically, a reduction in nonspecific binding was significant when a cell homogenate extract and a biotin-binding protein were added to a biological sample. Alternatively, addition of a cell homogenate extract prepared from cells genetically engineered to express a biotin-binding protein, instead of adding the biotin-binding protein, achieved substantially the same effect.

Based on the knowledge described above, the present invention provides a method of high-sensitive detection with reduced non-specific binding in a system in which a substance that specifically detects a substance to be detected is immobilized on a carrier through avidin-biotin binding.

The present invention includes the following nonlimiting embodiments.

[Embodiment 1]

A method for detecting a substance in a biological sample, which comprises:

1) providing a carrier on which a biotin-binding protein is bound and providing a biotinylated protein by biotinylating a protein that specifically binds to a substance to be detected;

2) binding the biotinylated protein to the carrier provided in step 1) through binding between biotin and the biotin-binding protein to produce a biotinylated protein-bound carrier;

3) mixing
  (a) a biological sample, and
  (b-i) a cell homogenate extract prepared from cells of the same species as that of the host cells used for expressing the biotin-binding protein, the protein that specifically binds to a substance to be detected, and/or the biotinylated protein in step 1), and a biotin-binding protein, or
  (b-ii) a cell homogenate extract prepared from cells of the same species as that of the host cells used for expressing the biotin-binding protein, the protein that specifically binds to a substance to be detected, and/or the biotinylated protein in step 1) and genetically engineered to express a biotin-binding protein,
and adding the mixture to the biotinylated protein-bound carrier produced in step 2); and 4) detecting a substance specifically bound to the biotinylated protein.

[Embodiment 2]

The method according to Embodiment 1, wherein step 3(b-i) in Embodiment 1 comprises adding a cell homogenate extract extracted from cells comprising any vector, as the cell homogenate extract.

[Embodiment 3]

The method according to Embodiment 1 or 2, wherein the biotin-binding protein is tamavidin or a variant thereof.

[Embodiment 4]

The method according to any one of Embodiments 1 to 3, wherein the biological sample is selected from the group consisting of blood, serum, cerebrospinal fluid, saliva, throat swab, sweat, urine, tear, lymph fluid, semen, ascites, and mother's milk.

[Embodiment 5]

An agent for diluting a biological sample, which comprises:

1) a cell homogenate extract and a biotin-binding protein, or 2) a cell homogenate extract prepared from cells genetically engineered to express a biotin-binding protein.

[Embodiment 6]

A kit for detecting a substance in a biological sample, which comprises:

A) a carrier on which a biotinylated protein, the biotinylated protein being a protein that specifically binds to a substance to be detected and has been biotinylated, is immobilized through binding between biotin and a biotin-binding protein; and an agent for diluting a biological sample, comprising B-i) a cell homogenate extract prepared from cells of the same species as that of the host cells used for expressing the biotin-binding protein, the protein that specifically binds to a substance to be detected, and/or the biotinylated protein in step A), and a biotin-binding protein, or B-ii) a cell homogenate extract prepared from cells of the same species as that of the host cells used for expressing the biotin-binding protein, the protein that specifically binds to a substance to be detected, and/or the biotinylated protein in step A) and genetically engineered to express a biotin-binding protein.

Advantages of the Invention

The method of the present invention enables high-sensitivity and stable detection, with a reduced background signal level, of a substance to be detected in a biological sample. In particular, the method of the present invention enables detection of a trace amount of substance which is present in a biological sample and, usually, cannot be readily detected or measured.

BRIEF DESCRIPTION OF THE DRAWINGS

FIG. 1A shows the result of Western blotting for detecting a SITH-1 protein, and FIG. 1B shows the result of activity staining for detecting a biotinylated protein.

E. coli BL21 (DE3) expressing the BioEase tag-fused SITH-1 protein was sonicated, and the resulting E. coli crude extract fraction was developed on SDS-PAGE (15% acrylamide gel) in such a manner that the amount of the total protein in each lane was 20 µg and was then transferred onto a PVDF membrane.

Figure 1:
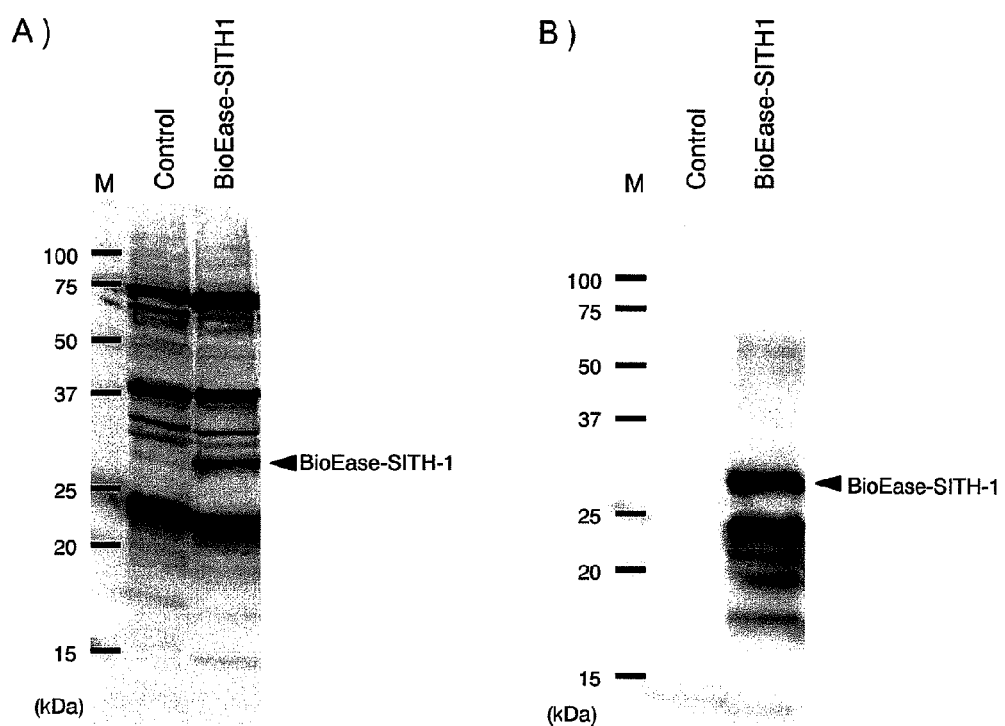
FIG. 1 shows expression of a BioEase tag (biotinylation tag)-fused SITH-1 protein. Specifically.

Specifically, FIG. 1A shows the results of staining with alkaline phosphatase (AP) after the reaction of an anti-SITH-1 antibody (1/1000 dilution) and an AP-labeled anti-rabbit IgG antibody (1/1000 dilution); and FIG. 1B shows the results of staining after the reaction of streptavidin-horseradish peroxidase (HRP) (1/1000 dilution). In both FIGS. 1A and 1B, extraction samples derived from E. coli containing an expression vector alone were used as controls. The positions of the BioEase tag-fused SITH-1 protein are shown by the arrows.

In the streptavidin-HRP staining in FIG. 1B, two thick bands were detected. Since no band corresponding to the lower band was detected with the anti-SITH-1 antibody in FIG. 1A, the lower band was believed to be a partially decomposed SITH-1 portion including the BioEase tag.

Figure 2:
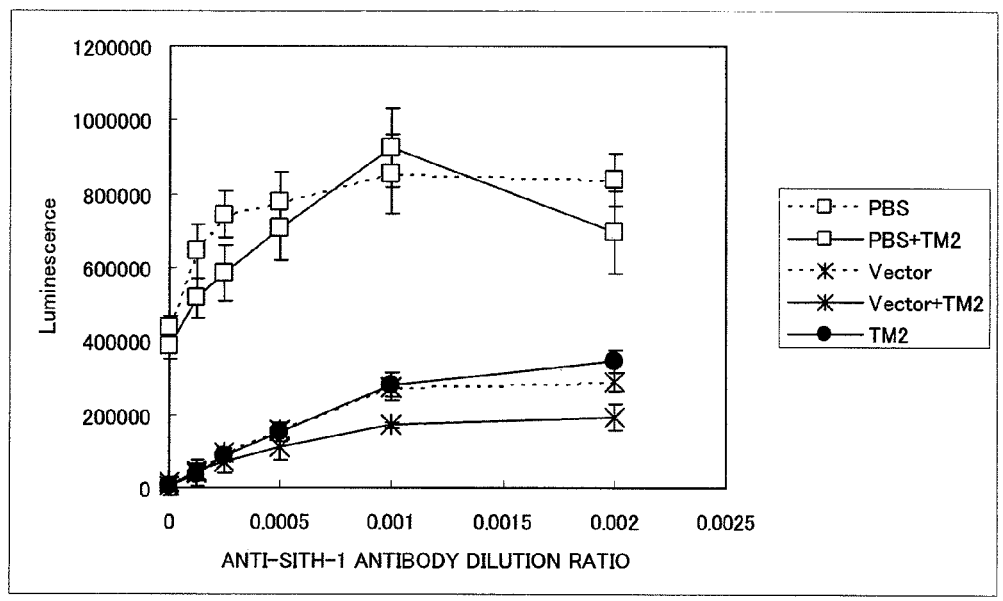

FIG. 2 is a graph showing the effects of various types of serum diluents on non-specific binding. Sections where serum was diluted with PBS are shown by open squares (dotted line), sections where serum was diluted with a PBS containing purified tamavidin 2 (TM2) are shown by open squares (solid line), sections where serum was diluted with an E. coli homogenate extract having only an expression vector are shown by asterisks (dotted line), sections where serum was diluted with a solution containing an E. coli homogenate extract having only an expression vector and purified TM2 are shown by asterisks (solid line), and section where serum was diluted with a TM2 expressing E. coli homogenate extract are shown by closed circles (solid line). The vertical axis (luminescence) of the graph represents the amount of the detected anti-SITH-1 antibody while the lateral axis represents the dilution ratio of the serially diluted anti-SITH-1 antibody.

Figure 3:
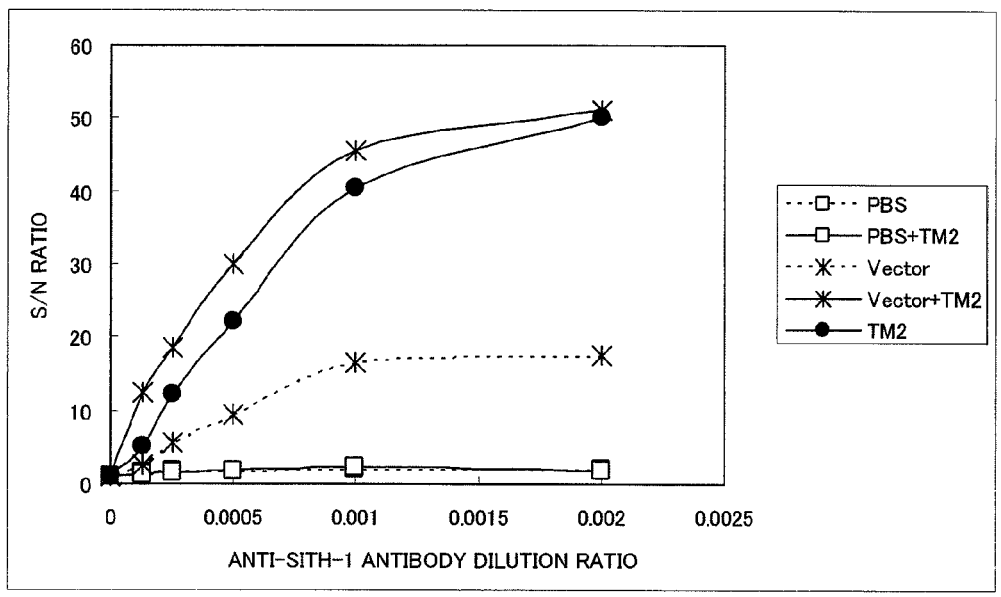

FIG. 3 is a graph showing S/N ratios at the respective dilution ratios of the anti-SITH-1 antibody obtained from the results shown in FIG. 2.

Sections where serum was diluted with PBS are shown by open squares (dotted line), sections where serum was diluted with a PBS containing purified tamavidin 2 (TM2) are shown by open squares (solid line), sections where serum was diluted with an E. coli homogenate extract having only an expression vector are shown by asterisks (dotted line), sections where serum was diluted with a solution containing an E. coli homogenate extract having only an expression vector and purified TM2 are shown by asterisks (solid line), and section where serum was diluted with a TM2 expressing E. coli homogenate extract are shown by closed circles (solid line).

Embodiments of the Invention

I. Method for Detecting a Substance in a Biological Sample

The method of the present invention comprises:

1) providing a carrier on which a biotin-binding protein is bound and providing a biotinylated protein by biotinylating a protein that specifically binds to a substance to be detected;

2) binding the biotinylated protein to the carrier provided in step 1) through binding between biotin and the biotin-binding protein to produce a biotinylated protein-bound carrier;

3) mixing
(a) a biological sample, and
(b-i) a cell homogenate extract prepared from cells of the same species as that of the host cells used for expressing the biotin-binding protein, the protein that specifically binds to a substance to be detected, and/or the biotinylated protein in step 1), and a biotin-binding protein, or
(b-ii) a cell homogenate extract prepared from cells of the same species as that of the host cells used for expressing the biotin-binding protein, the protein that specifically binds to a substance to be detected, and/or the biotinylated protein in step 1) and genetically engineered to express a biotin-binding protein, and adding the mixture to the biotinylated protein-bound carrier produced in step 2); and 4) detecting a substance specifically bound to the biotinylated protein.

1. Substance to be Detected in Biological Sample

The present invention relates to a method for detecting a substance in a biological sample.

Any biological sample that is expected to contain a substance as a detection target can be used in the present invention without limitation. Examples of the sample include cells and tissues collected from organisms and fragments thereof, for example, humors, more preferably, blood, serum, cerebrospinal fluid, saliva, throat swab, sweat, urine, tear, lymph fluid, semen, ascites, and mother's milk.

These humors may be used after dilution as needed. The dilution rate is, but not limited to, generally in the range of about 2 to about 10000 fold, preferably about 100 to 1000 fold. The solution for dilution may be any buffer solution, which may contain any proper blocking agent. Preferred blocking agents have high inhibitory effect on nonspecific binding, and can be selected from blocking agents well-known to persons skilled in the art, such as BSA and casein.

The substance to be detected in the present invention is any substance that is desired to be detected or measured in a biological sample, and preferred examples thereof include proteins such as antibodies and antigens and their fragments, peptides, nucleic acids, carbohydrates, and glycolipids and also include bacteria and viruses contained biological samples.

The present invention enables measurement of a trace amount of substance that is present in a biological sample and cannot be readily detected or accurately determined quantitatively by conventional methods. For example, if the substance to be detected is an antibody exhibiting a low antibody titer in a serum (e.g., a low antibody titer not detectable at 1000-fold dilution, but detectable at 100-fold dilution with difficulty), a low dilution rate of the serum is required. As a result, non-specific binding derived from serum components inevitably increases. Thus, no known method enables detection or determination of quantity for the antibody. In contrast, the method of the present invention can readily detect or accurately determine quantity of the antibody.

In the case where the substance to be detected in the present invention is an antibody, nonlimiting examples of the substance include antibodies against a small protein encoded by the intermediate transcript of HHV-6 (SITH-1). Other examples include antibodies against other antigens of herpes viruses, antibodies against virus-related antigens derived from, for example, cytomegaloviruses, hepatitis viruses, HIVs, HTLVs, measles viruses, and influenza viruses, antibodies against bacterium-related antigens derived from, for example, Helicobacter pylori, and antibodies against fungi-related antigens.

In the case where the substance to be detected in the present invention is an antigen, nonlimiting examples of the substance include antigens derived from the above-mentioned pathogens, cancer antigens, and prostate specific antigens.

SITH-1 Based on Description in PCT/JP2008/67300

(1) SITH-1 Protein and Nucleic Acid

The structures and functions of the SITH-1 protein and nucleic acid are disclosed in PCT/JP2008/67300, and the entity thereof is incorporated therein.

The SITH-1 is a factor involving latent infection with herpes viruses, and more particularly, a protein specifically expressed during latent infection with herpes viruses. The term "specifically expressed during latent infection with herpes viruses" therein refers to specific expression of genes or gene products derived from herpes viruses during latent infection (not productive infection) with herpes viruses in hosts infected with herpes viruses.

Examples of the SITH-1 protein and the nucleic acid include (a) a protein which has an amino acid sequence of SEQ ID NO: 1 and a nucleic acid encoding the protein.

The SITH-1 protein having the amino acid sequence of SEQ ID NO: 1, as described in Reference Example below, was isolated and identified as a protein that is specifically expressed during latent infection with human herpes viruses 6 (HHV-6). The SITH-1 protein is a protein having the amino acid sequence of SEQ ID NO: 1, composed of 159 amino acids, and having a molecular mass of about 17.5 kDa.

The SITH-1 protein is encoded by the nucleic acid of the SITH-1 gene. The cDNA of this SITH-1 gene, as shown in SEQ ID NO: 3, has a size of 1795 base pairs (about 1.79 kbp), the nucleotide sequence from the 954th to 956th being the initiation codon (Kozak ATG), while the nucleotide sequence from 1431st to 1433rd being the termination codon (TAA). Accordingly, the SITH-1 nucleic acid has a nucleotide sequence from 954th to 1430th as an open reading frame (ORF) in the nucleotide sequence of SEQ ID NO: 3, the ORF having a size of 477 base pairs (about 0.48 kbp). In the cDNA of the SITH-1, the nucleotide sequence representing the ORF region is shown in SEQ ID NO: 2. The nucleotide sequence of SEQ ID NO: 2 includes three bases of the stop codon.

The SITH-1 nucleic acid is always expressed in the cytoplasm of a cell latent-infected with HHV-6, but not in a productively infected cell. The nucleic acid encoding the SITH-1 protein is encoded by a DNA that is a complementary strand of the HHV-6 latent infection specific gene (H6LT), which has been reported to date, and its expression is enhanced in the intermediate stage of the latent infection with HHV-6. These facts demonstrate that the SITH-1 protein is a protein that is specifically expressed during latent infection with HHV-6.

The SITH-1 protein binds to a host protein, CAML (calcium-modulating cyclophilin ligand, Accession #: U18242) to increase the calcium concentration in the glial cells. The CAML is a protein that is known to be abundantly present in the brain and lymphocytes in the host living organism and increase the intracellular calcium concentration. It is considered that an increase in intracellular calcium concentration due to expression of the SITH-1 protein probably leads to activation of overall signaling in the latent-infected cells, and thus contributes to efficient reactivation of HHV-6.

It is known that the glial cells in the brain are latent-infected with HHV-6. When HHV-6 during the latent infection or at the intermediate stage which is a latent infection state with high activity expresses the SITH-1, the calcium concentration seems to increase in the glial cells. It is believed that an increase in intracellular calcium concentration in the brain is wedded to psychiatric disorders such as mood disorders (Riken Annual Report 2003).

The SITH-1 protein has a function that maintains activity to bind to the host protein, CAML, to increase the intracellular calcium concentration. Furthermore, expression of the SITH-1 protein in the glial cells, in which this protein seems to be most strongly expressed, in the brain can induce psychiatric disorders. Accordingly, the SITH-1 protein is believed to be expressed during the latent infection with herpes viruses or at the initial stage of reactivation of the herpes viruses to cause the host to have any psychiatric disorder.

(2) Antibody Against SITH-1

The antibody against the SITH-1 can be prepared as a polyclonal antibody or a monoclonal antibody from the SITH-1 protein, its variant, or a partial peptide thereof as antigen by a known process. Examples of the known process are described in documents such as Harlow et al., "Antibodies: A laboratory manual (Cold Spring Harbor Laboratory, New York (1988))" and Iwasaki et al., "Monoclonal Antibody: Hybridoma and ELISA, Kodansha (1991)". The resulting antibody can be used, for example, for detection and measurement of the SITH-1 protein.

The term "antibody" refers to immunoglobulins (IgA, IgD, IgE, IgG, IgM, and Fab fragments, F(ab')$_2$ fragments, and Fc fragments thereof). Examples of the antibody include, but not limited to, polyclonal antibodies, monoclonal antibodies, single-stranded antibodies, antiidiotype antibodies, and humanized antibodies.

The term "antibody recognizing the SITH-1 protein" includes complete molecules and antibody fragments (for example, Fab and F(ab')$_2$ fragments) that can specifically bind to the SITH-1 protein. Fab, F(ab')$_2$, and other fragments of the SITH-1 antibody can be used according to the method disclosed in the present specification or any known method. Such fragments can be typically produced by cleavage by proteolysis using an enzyme, e.g., a papain (yielding a Fab fragment) or pepsin (yielding an F(ab')$_2$ fragment).

It is believed that patients having mood disorders and individuals having potential mood disorders exhibit increased expression levels of the SITH-1 protein and thus increased SITH-1 antibody titers. In one embodiment of the present invention, detection of the SITH-1 antibody in a biological sample enables identification of patients having mood disorders and individuals having potential mood disorders.

2. Carrier on which Biotinylated Protein, the Biotinylated Protein being a Protein that Specifically Binds to a Substance to be Detected and has been Biotinylated, is Immobilized The present invention utilizes a carrier on which a biotinylated protein, the biotinylated protein being a protein that specifically binds to a substance to be detected and has been biotinylated, is bound by binding between biotin and a biotin-binding protein.

The carrier of the present invention can be produced by:

1) providing a carrier on which a biotin-binding protein is bound and providing a biotinylated protein by biotinylating a protein that specifically binds to a substance to be detected; and 2) binding the biotinylated protein to the carrier provided in step 1) through binding between biotin and the biotin-binding protein to produce a biotinylated protein-bound carrier.

"Biotin" is a generic name of D-[(+)-cis-hexahydro-2-oxo-1H-thieno-(3,4)-imidazole-4-valeric acid]. It is one of water-soluble vitamin categorized into a vitamin B group, and is also referred to as vitamin B$_7$, vitamin H, or coenzyme R. Biotin very strongly binds to avidin, one of the glycoproteins contained in egg white, so that its absorption is precluded. Thus, large dose of uncooked egg white may cause biotin deficiency disease in some cases.

The term "biotin" throughout the specification includes iminobiotin (Hofmann et al., (1980), Proc Natl Acad Sci USA, 77: 4666-4668), desthiobiotin (Hirsch et al., (2002), Anal Biochem, 308: 343-357), and biotin analogs such as biocytin and biotin sulfoxide, in addition to the biotin described above.

Systems using biotin-avidin (biotin-binding protein) complexes are widely used in the fields of biochemistry, molecular biology, tissue immunology, DNA analysis, and clinical assay.

The present invention includes immobilization of a protein that specifically binds to a substance to be detected to a carrier utilizing binding between biotin and a biotin-binding protein. In the present invention, "binding between biotin and a biotin-binding protein" may be referred to as "avidin-biotin binding".

Biotin-Binding Protein

Any protein that strongly binds to biotin can be preferably used as the biotin-binding protein, and examples thereof include avidin, streptavidin, neutravidin, AVR protein (Biochem. J., (2002), 363: 609-617), bradavidin (J. Biol. Chem., (2005), 280: 13250-13255), rhizavidin (Biochem. J., (2007), 405: 397-405), tamavidin (WO2002/072817), and variants thereof. The dissociation constant (KD) with biotin is preferably $10^{-8}$ M or less, more preferably $10^{-10}$ M or less, more preferably $10^{-12}$ M or less. The biotin-binding protein that is added to a sample to be tested will be described below.

Particularly preferred biotin-binding proteins are tamavidin and variants thereof, which can be highly expressed in *E. coli*. Tamavidin is a biotin-binding protein discovered in an edible mushroom, *Pleurotus cornucopiae* (WO2002/072817, Takakura et al., (2009), FEBS J, 276: 1383-1397). An example of the variants of tamavidin is tamavidin exhibiting high binding capability and low non-specific binding characteristics (PCT/JP2009/64302).

The term "tamavidin" in the present invention refers to tamavidin 1 (TM1), tamavidin 2 (TM2), or a variant thereof. Specifically, tamavidin of the present invention may be typically a protein having the amino acid sequence of SEQ ID NO: 5 or SEQ ID NO: 7, or a protein encoded by a nucleic acid having the nucleotide sequence of SEQ ID NO: 4 or SEQ ID NO: 6. Alternatively, tamavidin of the present invention may be a protein that is a variant of a protein having the amino acid sequence of SEQ ID NO: 5 or SEQ ID NO: 7 or a protein encoded by a nucleic acid having the nucleotide sequence of SEQ ID NO: 4 or SEQ ID NO: 6 and having biotin binding capability similar to that of tamavidin 1 or 2 or high binding capability and low non-specific binding characteristics. Throughout the specification, tamavidin 1, tamavidin 2, and variants thereof may be collectively referred to as tamavidin.

The variant of tamavidin 1 or 2 may be a protein having an amino acid sequence comprising deletion, substitution, insertion, and/or addition of one or more amino acids in the amino acid sequence of SEQ ID NO: 5 or 7 and having biotin binding capability similar to that of tamavidin 1 or 2. The substitution may be conservative substitution. The conservative substitution refers to replacement of a specific amino acid residue with any residue having similar physicochemical features. Nonlimiting examples of the conservative substitution include substitutions between amino acid residues containing aliphatic groups, such as mutual substitution between Ile, Val, Leu, and Ala; and substitutions between polar residues, such as mutual substitution between Lys and Arg, between Glu and Asp, and between Gln and Asn.

The variant by deletion, substitution, insertion, and/or addition of an amino acid or amino acids can be produced by a known technique such as site-specific mutagenesis (e.g., see Nucleic Acid Research, Vol. 10, No. 20, pp. 6487-6500, 1982, which is incorporated herein in its entirety) to a DNA encoding a wild-type protein. Throughout the specification, the term "one or more amino acids" herein refers to an amino acid or amino acids that can be deleted, substituted, inserted, and/or added by preferably site-specific mutagenesis. In addition, the term "one or more amino acids" herein may refer to one or several amino acids. The "one or more amino acids" refers to, but not limited to, 50 or less, preferably 40 or less, 30 or less, 20 or less, 10 or less, 8 or less, 5 or less, or 3 or less amino acids.

The variant of tamavidin 1 or 2 may also be a protein including an amino acid sequence having a homology of 60% or more, preferably 65% or more, 70% or more, 75% or more, 80% or more, 85% or more, 90% or more, 95% or more, 96% or more, 97% or more, 98% or more, or 99% or more, more preferably 99.3% or more to the amino acid sequence of SEQ ID NO: 5 or SEQ ID NO: 7 and having biotin binding capability similar to that of tamavidin 1 or 2 or high binding capability and low non-specific binding characteristics.

The percent identity between two amino acid sequences may be determined by visual inspection and mathematical calculation. Alternatively, the percent identity between two protein sequences may be determined through comparison of sequence information using a GAP computer program available from the University of Wisconsin Genetics Computer Group (UWGCG) based on the algorithm by Needleman, S. B. and Wunsch, C. D. (J. Mol. Biol., 48: 443-453, 1970). Preferred default parameters of the GAP program include: (1) scoring matrix: blosum62 described in Henikoff, S, and Henikoff, J. G, (Proc. Natl. Acad. Sci. USA, 89: 10915-10919, 1992); (2) 12 gap weights; (3) 4 gap length weights; and (4) no penalty for terminal gaps.

Any other program used by persons skilled in the art may also be used for comparison of the sequences. The percent identity can be determined by, for example, comparison with the sequence information using a BLAST program described in Altschul et. al., (Nucl. Acids. Res., 25, pp. 3389-3402, 1997). This program is available from the websites of National Center for Biotechnology Information (NCBI) or DNA Data Bank of Japan (DDBJ) on the Internet. The conditions (parameters) for identity search by the BLAST program is described in detail on these sites. Although these parameters can be partly modified if necessary, search is generally carried out using the default values. Alternatively, the percent identity between two amino acid sequences may be determined using a program such as genetic information processing software GENETYX Ver. 7 (available from GENETYX CORPORATION) or FASTA algorithm, wherein search may be carried out using the default values.

The percent identity between two nucleotide sequences can be determined by visual inspection and mathematical calculation. Preferably, such comparison is carried out through comparison of sequence information using a computer program. A particularly preferred computer program is a version 10.0 program "GAP", Wisconsin package of Genetics Computer Group (GCG, Madison, Wis.) (Devereux, et al., 1984, Nucl. Acids Res., 12: 387). The use of the "GAP" program enables comparison between two amino acid sequences and comparison between a nucleotide sequence and an amino acid sequence, in addition to comparison of two nucleotide sequences.

The "biotin-binding protein" to be immobilized to a carrier is used for preparing a biotinylated protein-bound carrier by binding the biotinylated protein to the carrier through binding between biotin and the biotin-binding protein. Accordingly, it is preferred that the biotin binding activity of a variant of tamavidin 1 or 2 is not significantly decreased compared to that in the case of forming the biotinylated proteins using these wild-types, but it is not limiting.

Accordingly, non-limitingly, in the variant of tamavidin 1, preferably, N14, S18, Y34, S36, S78, W82, W98, W110, and D118 in the amino acid sequence of SEQ ID NO: 5 are not modified. Note that the notation, for example, Y34 indicates the 34th tyrosine residue of the amino acid sequence of SEQ ID NO: 5. Alternatively, in the modification of these amino acid residues, the amino acid is preferably replaced with one having a similar property or structure. For example, asparagine (N14) is replaced with glutamine (Q) or aspartic acid (D), preferably aspartic acid; serine (S18, S36, or S78) is replaced with threonine (T) or tyrosine (Y), preferably threonine; tyrosine (Y34) is replaced with serine (S), threonine (T), or phenylalanine (F), preferably phenylalanine; tryptophan (W82, W98, or W110) is replaced with phenylalanine (F); and aspartic acid (D118) is replaced with glutamic acid (E) or asparagine (N), preferably asparagine.

In the variant of tamavidin 2, preferably, four tryptophan residues (W69, W80, W96, and W108) in the amino acid sequence of SEQ ID NO: 7 are not modified. Alternatively, when these amino acid residues are modified, the amino acid is preferably replaced with one having a similar property or structure, for example, phenylalanine (F). In addition, it is desirable that amino acid residues (N14, S18, Y34, S36, S76, T78, and D116) that probably interact directly with biotin are also not modified. Alternatively, in the modification of these amino acid residues, the amino acid is preferably replaced with one having a similar property or structure in order to maintain the binding with biotin. For example, asparagine (N14) is replaced with glutamine (Q) or aspartic acid (D), preferably aspartic acid; aspartic acid (D40) is replaced with asparagine (N); serine (S18, S36, or S76) is replaced with threonine (T) or tyrosine (Y), preferably threonine; tyrosine (Y34) is replaced with serine (S), threonine (T), or phenylalanine (F), preferably phenylalanine; threonine (T78) is replaced with serine (S) or tyrosine (Y), preferably serine; and aspartic acid (D116) is replaced with glutamic acid (E) or asparagine (N), preferably asparagine.

Preferred variants of tamavidin in the present invention include the following variants (PCT/JP2009/64302).

The tamavidin variant is a modified biotin-binding protein that has the amino acid sequence of SEQ ID NO: 7 or an amino acid sequence comprising one to several amino acid mutations in this sequence or having a homology of at least 80% with this sequence and that shows biotin binding activity, wherein one or more residues selected from the group consisting of:

1) the arginine residue at the 104th site of SEQ ID NO: 7;
2) the lysine residue at the 141st site of SEQ ID NO: 7;
3) the lysine residue at the 26th site of SEQ ID NO: 7; and
4) the lysine residue at the 73rd site of SEQ ID NO: 7; are replaced with acidic or neutral amino acid residues.

More preferably, the tamavidin variant is a modified biotin-binding protein selected from the group consisting of:

a modified biotin-binding protein (R104E-K141E) in which the arginine residue at the 104th site is replaced with a glutamic acid residue, and the lysine residue at the 141st site is replaced with a glutamic acid residue, in SEQ ID NO: 7;

a modified biotin-binding protein (D40N-R104E) in which the aspartic acid residue at the 40th site is replaced with a asparagine residue, and the arginine residue at the 104th site is replaced with a glutamic acid residue, in SEQ ID NO: 7;

a modified biotin-binding protein (D40N-K141E) in which the aspartic acid residue at the 40th site is replaced with a asparagine residue, and the lysine residue at the 141st site is replaced with a glutamic acid residue, in SEQ ID NO: 7; and a modified biotin-binding protein (D40N-R104E-K141E) in which the aspartic acid residue at the 40th site is replaced with a asparagine residue, the arginine residue at the 104th site is replaced with a glutamic acid residue, and the lysine residue at the 141st site is replaced with a glutamic acid residue, in SEQ ID NO: 7.

Biotin-binding Protein-bound Carrier

Examples of materials for the solid carrier include, but not limited to, cellulose, Teflon (registered trademark), nitrocellulose, agarose, highly cross-linked spherical agarose, dextran, chitosan, polystyrene, polyacrylamide, polyesters, polycarbonates, polyamides, polypropylene, nylons, polydivinylidene difluoride, latex, polystyrene latex, silica, glass, glass fiber, gold, platinum, silver, copper, iron, stainless steel, ferrite, silicon wafers, polyethylene, polyethyleneimine, poly(lactic acid), resins, polysaccharides, proteins such as albumin, carbon, and combination thereof. Preferred materials have a certain level of strength, a stable composition, and reduced non-specific bindings.

Examples of the shape of the solid carrier include, but not limited to, beads, magnetic beads, thin films, capillary tubes, filters, plates, microplates, carbon nanotubes, and censor chips. Flat solid carriers such as thin films and plates may be provided with pits, grooves, or filter bottoms, as is known in the art.

In an embodiment of the invention, beads may have a spherical diameter in the range of about 25 nm to about 1 mm. In a preferred embodiment, the beads may have a diameter in the range of about 50 nm to about 10 µm. The size of the beads may be selected depending on the specific application.

Without any limitation, for example, in the case that high sensitivity for detection is desired, beads as described above can preferably be used as the solid carrier in the view point that the beads provide high contacting frequency between the target substance to be detected and the substance that specifically binds to the target substance, and that cleaning operation thereof is easy.

As a method for producing a carrier on which a biotin-binding protein is bound, the biotin-binding protein may be directly bound to the carrier, or a carrier on which a biotin-binding protein is immobilized in advance may be purchased. Alternatively, a biotin-binding protein may be bound to a biotinylated carrier through binding between the biotin and the biotin-binding protein.

Direct binding of the biotin-binding protein can be performed, for example, by hydrophobic bonding or covalent bonding. Alternatively, the biotin-binding protein may be directly bound and immobilized to a microplate such as NEW ELISA Plate kit (Sumitomo Bakelite Co., Ltd.) according to the instructions attached to the kit. Avidin and streptavidin are commercially available from, for example, Sigma.

In the case of the use of hydrophobic bonding, binding is achieved by interaction between the hydrophobic surface of the carrier and the hydrophobic moiety of the biotin-binding protein. Specifically, a solution of the biotin-binding protein is put into direct contact with the surface of a carrier such as a microplate (e.g., but not limited to, Nunc-Immuno™ Plate (Nunc), SpectraPlate-96 HB (Perkin Elmer), or Reacti-Bind™ 96-Well Plates Corner Notch (PIERCE)), and is allowed to stand for a predetermined time, so that the biotin-binding protein is bound and immobilized on the carrier by the interaction between the hydrophobic moiety of the biotin-binding protein and the hydrophobic portion of the carrier.

Meanwhile, in the case of the covalent bonding, functional groups are provided on the surface of a carrier so as to be bound to the functional groups in the biotin-binding protein. For such binding, a variety of carriers provided with various functional groups on the surfaces are commercially available and can be preferably used. Nonlimiting examples of such microplates provided with functional groups on the surface include maleic anhydride plates, e.g., Reacti-Bind™ Maleic Anhydride Activated Polystyrene 96-Well Plates (PIERCE); activated amino group plates, e.g., Immobilizer™-Amino Modules/Plates (Nunc); and carboxyl group plates, e.g., ELISA plate MS-8796F (96 wells, type C, flat bottom, Carbo) (Sumitomo Bakelite CO., Ltd). Nonlimiting examples of microbeads provided with functional groups on the surfaces include highly cross-linked agarose beads, e.g., Sepharose™ (GE Healthcare Biosciences); and magnetic beads, e.g., Dynabeads™ (Dynal). Linking between the biotin-binding protein and the solid carrier may be performed according to the instructions attached to the carrier.

Specifically, but not limited to, a protein can be bound to a solid carrier by a coupling process known to persons skilled in the art as follows. For example, a biotin-binding protein can be linked to a solid carrier by a coupling reaction of carboxyl groups exposed on the surface of the solid carrier by modification and amino groups of the biotin-binding protein in the presence of a cross-linking reagent, 1-ethyl-3-(3-dimethylaminopropyl)carbodiimide (EDC). Alternatively, a biotin-binding protein is applied to a solid carrier having a surface active esterified with N-hydroxysuccinimide (NHS) in a buffer solution not containing a primary amino group and having a pH of 6.5 to 9 to bind the carboxyl groups on the solid carrier surface and the amino groups of the biotin-binding protein. Alternatively, amino groups of a biotin-binding protein can be bound to amino groups of a solid carrier surface using a cross-linking reagent, bis[sulfosuccinimidyl]suberate (BS3) or disuccinimidyl suberate (DSS), or thiol groups of a biotin-binding protein can be bound to amino groups of a solid carrier surface using a cross-linking reagent, N-succinimidyl-3 [2-pyridyldithio]propionate (SPDP) or N-(4-maleimidobutyryloxy)succinimide (GMBS).

Examples of a commercially available carrier on which a biotin-binding protein is immobilized include, but not limited to, microplates such as Reacti-Bind™ Streptavidin Coated Plates (PIERCE) and Nunc Streptavidin Coated 96 Micro Well™ Plates (Nalge Nunc); and magnetic beads such as Dynabeads M-280 Streptavidin (Dynal) and MagnaBind™ Streptavidin Beads (PIERCE).

The biotin-binding protein can also be bound to a biotinylated carrier through avidin-biotin binding as described above. That is, a biotin-binding protein is bound to a biotinylated carrier utilizing the fact that many of biotin-binding proteins are tetramers, and then a biotinylated protein is further bound.

An exemplary method of binding biotin to the carrier involves use of a biotinylation reagent. Examples of the biotinylation reagent include, but not limited to, EZ-Link (registered trademark) Sulfo-NHS-Biotin (the length of the linker: 13.5 angstroms, the reactive group: primary amine, hereinafter the same order), EZ-Link (registered trademark) Sulfo-NHS-LC-Biotin (22.4 angstroms, primary amine), EZ-Link (registered trademark) Sulfo-NHS-LCLC-Biotin (30.5 angstroms, primary amine), EZ-Link (registered trademark) PFP-Biotin (9.6 angstroms, amine), EZ-Link (registered trademark) Maleimide-$PEO_2$-Biotin (29.1 angstroms, thiol group), EZ-Link (registered trademark) Biotin-$PEO_2$ Amine (20.4 angstroms, carboxyl group), EZ-Link (registered trademark) Biotin-$PEO_3$-LC Amine (22.9 angstroms, carboxyl group), EZ-Link (registered trademark) Biotin-Hydrazide (15.7 angstroms, aldehyde group), EZ-Link (registered trademark) Biotin-LC-Hydrazide (24.7 angstroms, aldehyde group), and EZ-Link (registered trademark) NHS-Iminobiotin (13.5 angstroms, primary amine), which are available from PIERCE.

Using these biotinylation reagent, biotin can be bound to a desired carrier such a microplate, microbeads, or a sensor chip by any known process. For example, various carriers having functional groups, such as amino, carboxyl, thiol, tosyl, epoxy, and maleimide groups, and activated ester (for example, magnetic beads, Sepharose beads, agarose beads, latex beads, and microtiter plates) can be used. For example, in the case of the use of a biotinylation reagent containing NHS ester, the reagent may be dissolved in an organic solvent such as a dimethyl sulfoxide (DMSO) or phosphate buffer solution of pH of 7 to 9, and then may be added to an immobilization carrier having amino groups to bind biotin thereto. In the case of the use of a biotinylation reagent containing amino groups, the carboxyl groups on the immobilization carrier may be converted to activated ester using carbodiimide such as 1-ethyl-3-(3-dimethylaminopropyl)carbodiimide hydrochloride (EDC), followed by addition of a biotinylation reagent dissolved in a buffer solution of pH of about 5 to bind biotin to the carrier. The biotinylated immobilization carrier is preferably blocked with BSA after inactivation of unreacted functional groups.

Commercially available biotinylated carriers can also be used. Examples of the biotinylated microplates include, but not limited to, Reacti-Bind™ Biotin Coated Polystyrene Plates (PIERCE). Examples of the biotinylated microbeads include, but not limited to, magnetic beads, such as BioMag Biotin (available from Polysciences); magnetic nanobeads, such as nanomag (registered trademark)-D biotin and nanomag(registered trademark)-silica biotin available from Corefront; polystyrene microbeads, such as Beadlyte (registered trademark) Biotin Beads (available from Upstate); agarose, such as Biotin Agarose and 2-iminobiotin-Agarose available from Sigma; and highly cross-linked agarose, such as Biotin-Sepharose (available from Biosearch Technologies, Inc.).

The length of the linker binding the carrier to biotin is preferably at least 5 angstroms and more preferably at least 13.5 angstroms.

A biotin-binding protein-bound carrier can be produced by putting a biotin-binding protein into contact with such a biotinylated carrier.

Biotinylated Protein

In the present invention, a biotinylated protein may be produced by binding biotin to a protein that specifically binds to a substance to be detected, and this biotinylated protein may be bound to a carrier through binding between biotin and a biotin-binding protein.

The method of producing a biotinylated protein is not particularly limited, but biotin may be bound to any protein that specifically binds to a substance to be detected using a biotin labeling kit (e.g., but not limited to, EZ-Link (registered trademark) NHS-Lc-Biotin (PIERCE) and Biotin Labeling Kit-$NH_2$ (DOJINDO MOLECULAR TECHNOLOGIES INC.)). Alternatively, a biotinylated protein may be produced by fusing a gene of a protein that specifically binds to a substance to be detected with a DNA encoding a peptide comprising a biotinylated sequence, constructing a vector expressing the fused gene, and expressing the biotinylated protein as a fused protein with a biotinylated sequence in any host (Schwarz et al., (1988). J. Biol. Chem., 263: 9640-9645). Nonlimiting examples of such vectors include vectors including BioEase™ tags available from Invitrogen (Example 1 of this specification). Among them, a pcDNA™ 6 vector is used for mammalian cell expression, a pET 104 vector for *E. coli* expression, and a pMT/BioEase vector for *Drosophila* expression.

Furthermore, the method used in the biotinylation of the carrier described above also can be preferably used for biotinylation of a desired protein. That is, a method using a biotinylation reagent can be employed. Examples of the biotinylation reagent include, but not limited to, EZ-Link (registered trademark) Sulfo-NHS-Biotin (the length of the linker: 13.5 angstroms, the reactive group: primary amine, hereinafter the same order), EZ-Link (registered trademark) Sulfo-NHS-LC-Biotin (22.4 angstroms, primary amine), EZ-Link (registered trademark) Sulfo-NHS-LCLC-Biotin (30.5 angstroms, primary amine), EZ-Link (registered trademark) PFP-Biotin (9.6 angstroms, amine), EZ-Link (registered trademark) Maleimide-PEO$_2$-Biotin (29.1 angstroms, thiol group), EZ-Link ( registered trademark) Biotin-PEO$_2$ Amine (20.4 angstroms, carboxyl group), EZ-Link (registered trademark) Biotin-PEO$_3$-LC Amine (22.9 angstroms, carboxyl group), EZ-Link (registered trademark) Biotin-Hydrazide (15.7 angstroms, aldehyde group), EZ-Link (registered trademark) Biotin-LC-Hydrazide (24.7 angstroms, aldehyde group), and EZ-Link (registered trademark) NHS-Iminobiotin (13.5 angstroms, primary amine), which are commercially available from PIERCE.

Using such a biotinylation reagent, biotin can be bound to a desired protein through any known process.

For example, in the case of the use of a biotinylation reagent containing NHS ester, biotin is dissolved in an organic solvent such as a dimethyl sulfoxide (DMSO) or phosphate buffer solution (pH: 7 to 9) and then may be added to a desired protein to be bound to biotin. Alternatively, in the case of the use of a biotinylation reagent containing amino groups, the carboxyl group of a desired protein is converted into activated ester with carbodiimide such as 1-ethyl-3-(3-dimethylaminopropyl)carbodiimide hydroxychloride (EDC), followed by addition of a biotinylation reagent in a buffer solution (pH: about 5) to bind biotin to the desired protein.

In the case of producing a biotinylated protein using such a biotinylation reagent, the protein that is specifically binds to a substance to be detected is preferably purified in advance. The purification may be performed for an organism from which the protein is originally derived or may be started after expression of the protein by using genetic engineering in desired host cells by cloning a gene encoding the protein into an expression vector. Examples of the host cells include mammalian cells (e.g., but not limited to, cells derived from primates such as human and monkey; rodents such as mouse, rat, Chinese hamster; and canine), insect cells (expression systems utilizing baculovirus and *Drosophila* system), yeast, *E. coli*, plants, and *Bacillus subtilis*. Preferred is *E. coli*. In addition, established culture cell systems, for example, HEK293, HeLa, HepG2, and 293T for human cells; CHO, NIH3T3, and PC12 for rodent cells; COS-1, COS-7, MDCK, and Vero for other mammalian cells; and Sf9 and S2 for insect cells can be preferably used. Alternatively, the protein can be expressed using cell-free expression systems using, for example, a wheat germ extract or an insect cell extract.

Persons skilled in the art can appropriately select expression vectors suitable for host cells used.

The expressed protein can be purified by any method well known to persons skilled in the art, for example, a combination of ordinary chromatographic processes, such as ion-exchange chromatography, hydrophobic chromatography, and gel-permeation chromatography or use of a tag sequence for purification. In such a case, the protein that specifically binds to a substance to be detected may be expressed in any host cells such as *E. coli* or mammalian cells as a fusion protein with, for example, glutathione-S-transferase, a maltose-binding protein, a cellulose-binding protein, a chitin-binding protein, or a thioredoxin-binding protein, and the resulting protein may be purified by affinity with glutathione, maltose, cellulose, chitin, or thioredoxin, respectively (for example, using a glutathione-immobilized column). Preliminary introduction of the recognition site of a protease into the fusion site with the protein that specifically binds to a substance to be detected enables removal of the tag sequence by treating with the protease after purification. As the protease, those well known to persons skilled in the art, such as enterokinase and Factor Xa, can be used. Alternatively, the protein may be purified using a HisTag or Strep(II)-Tag through an ionized nickel or Strep-Tactin column. In order to enhance the purity, multiple tags may be fused to the protein that specifically binds to a substance to be detected so that the protein is purified by a combined process. For example, a HisTag and a biotinylated sequence such as BioEASE™ (Invitrogen) may be fused to the terminal of the protein that specifically binds to a substance to be detected to express a recombinant protein in host cells, and then purification may be performed through a nickel column and then through a low affinity avidin or low affinity streptavidin (e.g., SA mutein, Roche) column.

Binding of Biotinylated Protein to Carrier

In the present invention, a protein can be bound to a carrier through avidin-biotin binding by providing a biotin-binding protein-bound carrier and a biotinylated protein and putting them into contact with each other.

A crude cell homogenate extract containing a biotinylated protein is prepared in a total protein content of, but not limited to, 0.1 mg/mL to 5 mg/mL, preferably 0.2 mg/mL to 2 mg/mL. This extract is put into contact with a carrier to which biotin-binding protein is bound at 10° C. to 40° C., preferably 20° C. to 30° C., for 5 min to 2 hr, preferably 30 min to 1 hr. With this procedure, the biotinylated protein is bound to the biotin-binding protein-bound carrier. Subsequently, excessive crude cell homogenate extract is preferably washed out in a buffer solution such as PBS or TBS containing 0.05% to 1%, preferably 0.1% to 0.3%, of a surfactant such as Tween 20.

In the case of performing the binding of a biotinylated protein by putting a crude cell homogenate extract into contact with a carrier, actually, purification and immobilization are simultaneously achieved. Accordingly, in this case, a separate purification process is unnecessary.

Alternatively, a purified biotinylated protein in a concentration of 0.1 µg/mL to 5 µg/mL may be put into contact with a carrier to which a biotin-binding protein is bound.

3. Addition of Biological Sample to Biotinylated Protein-Bound Carrier

The method of the present invention includes, in step 3), mixing
  (a) a biological sample, and
  (b) a cell homogenate extract prepared from cells of the same species as that of the host cells used for expressing the biotin-binding protein, the protein that specifically binds to a substance to be detected, and/or the biotinylated protein in step 1)
and adding the mixture to the biotinylated protein-bound carrier produced in step 2).

Addition of Cell Homogenate Extract

In a method of detection using a carrier, generally known approaches for reducing non-specific binding which causes background signals are, for example, addition of a bacterium homogenate extract to a reagent for detection (JP No. S59-99257 A (1984)); addition of a culture component of host cells to a sample, where a vector of the same species as that used in production of a recombinant protein capable of specifically binding to a substance to be detected and containing no gene encoding the protein is introduced into the host cells (JP No. H8-43392 A (1996)); and heat treatment of an aqueous extract from cells of the same species as that producing a recombinant protein capable of specifically binding to a substance to be detected and not containing this protein, and addition of its water-soluble fraction to a sample (JP Publication No. 2004-301646 A).

The present inventors have diligently studied and, as a result, have arrived at a method of obtaining a noticeable effect in a system in which a protein for detection is bound to a carrier through binding between biotin and a biotin-binding protein. Specifically, the present inventors have discovered that it is preferable to put a substance to be detected into contact with a carrier in the presence of both a cell homogenate extract and a biotin-binding protein.

Cells from which a cell homogenate extract is derived are not preferably limited, and examples thereof are *E. coli* cells, yeast cells, mammalian cells, insect cells, and plant cells. Preferred cells are the same species as that of host cells used for expressing the biotin-binding protein, the protein that specifically binds to a substance to be detected, and/or the biotinylated protein. For example, in the case of preparing the biotin-binding protein, the protein that specifically binds to a substance to be detected, and/or the biotinylated protein using *E. coli*, it is desirable to also prepare the cell homogenate extract from *E. coli*. In the case of expressing the biotin-binding protein, the protein that specifically binds to a substance to be detected, and/or the biotinylated protein in a cell-free system, the cell homogenate extract used can be used directly or as a suspension in a desired buffer solution. Furthermore, two or more cell homogenate extracts may be used according to the combination of host cells used for expressing the biotin-binding protein, the protein that specifically binds to a substance to be detected, and/or the biotinylated protein The biotin-binding protein and/or the protein that specifically binds to a substance to be detected may be extracted and purified from cells originally having these proteins, instead of those being genetically expressed. For example, in the case of using tamavidin as a biotin-binding protein, a cell homogenate extract of *Pleurotus cornucopiae* can be used. Accordingly, the cell extract of the present invention includes a homogenate extract of cells that originally contain a biotin-binding protein and/or a protein that specifically binds to a substance to be detected.

The cell used for preparation of the cell homogenate extract may contain any vector, preferably an empty vector. The empty vector is of the same species as that of the vector used in expression of the biotin-binding protein, the protein that specifically binds to a substance to be detected, and/or the biotinylated protein and does not contain a gene that encodes these proteins. The empty vector may further contain any nucleic acid. Alternatively, the empty vector may be different from the vector used in expression of the biotin-binding protein, the protein that specifically binds to a substance to be detected, and/or the biotinylated protein.

As the cell homogenate extract, any components derived from cells can be used without limitation. For example, protein components, carbohydrate components, lipid components of cells, or mixture thereof can be used. Preferably, soluble extracts of cells can be used.

The cell homogenate extract can be prepared by a variety of processes without limitation. In general, cells cultured in a proper culture medium are homogenized or solubilized by a physical means such as ultrasonication, a chemical means using a surfactant, or enzyme treatment, and then an extract can be prepared as soluble components isolated by centrifugation or filtration. In order to prolong the storage life, preferably, the clear liquid prepared by, for example, centrifugation or filtration is mixed with, for example, a protease inhibitor or is heated, for example, in an autoclave to suppress or deactivate various enzymes and other active components derived from cells. The concentration of the cell homogenate extract can be varied depending on the strength of occurring non-specific reaction and may be appropriately set in a range sufficient to absorb the non-specific reaction.

As a nonlimiting specific example of the method for preparing a cell homogenate extract, in the case of *E. coli* cells, *E. coli* cells (which may contain a vector optionally containing a gene encoding a biotin-binding protein) are inoculated into an LB culture medium containing an antibiotic; shake culture is performed at 15° C. to 37° C., preferably at 25° C. to 37° C., until the absorbance at OD 600 reaches 0.1 to 2, preferably 0.25 to 1, more preferably 0.4 to 0.6; 0.01 to 5 mM, preferably 0.1 to 1 mM IPTG is added thereto; and then shake culture is further performed at 15° C. to 37° C., preferably at 25° C. to 37° C., for 2 to 24 hr, preferably for 4 to 16 hr. The bacterial cells are collected by centrifugation from the culture solution, are suspended in a desired buffer solution, and are homogenized. After centrifugation of the homogenized solution, the supernatant is collected as a crude *E. coli* extract.

When a biological sample is mixed with a crude cell homogenate extract, the sample is reacted with, but not limited to, a crude cell homogenate extract that has been prepared with a desired buffer (which may contain, for example, BSA, casein, or a commercially available blocking agent) into a total protein concentration of 0.05 to 5 mg/mL, preferably 0.5 to 5 mg/mL, at 10° C. to 30° C., preferably, 20° C. to 30° C. for 1 min to 4 hr, preferably 10 min to 1 hr. In the case of a serum as the biological sample, the serum is generally diluted with the crude cell homogenate extract to 10 to 10000-fold, preferably 100 to 1000-fold, more preferably 100 to 500-fold.

Addition of Biotin-Binding Protein

In the method of the present invention, the background signal level can be finally suppressed by adding a biotin-binding protein to a biological sample.

Such a biotin-binding protein may be the same as or different from the biotin-binding protein bound to the carrier. Either the wild type or a variant may be used. The biotin-binding activity of the variant may be equivalent, higher, or lower compared to that of the wild type. In an embodiment of the addition, powder of a biotin-binding protein (which may be a naturally occurring protein or may be expressed by genetic engineering) may be added to the sample directly or after its dissolution in a proper liquid. For example, in another embodiment, a mixture of a sample and a cell homogenate extract may be treated with a carrier to which the biotin-binding protein is immobilized (for example, the mixture is passed through a column) (step b-i), instead of direct addition of the biotin-binding protein to the sample.

In the case of adding the biotin-binding protein to a crude cell homogenate extract, the final concentration of the added biotin-binding protein is, but not limited to, 1 to 500 µg/mL, preferably 10 to 100 µg/mL. The concentration of the biotin-binding protein when it is genetically engineered to be expressed in the cells may also substantially be the same as above, but any other concentration is acceptable.

Alternatively, a gene encoding a biotin-binding protein is introduced into host cells and is expressed, and a cell extract containing a biotin-binding protein obtained by homogenizing the host cells may be used (step b-ii). In this case, the biotin-binding protein may be expressed in a desired host by a method well known to persons skilled in the art. In the case where a desired protein that specifically binds to a substance to be detected and/or a desired biotinylated protein is expressed by genetic engineering, the cell homogenate extract is preferably derived from the same species as that of the host.

In the case of the host being *E. coli*, a gene encoding the biotin-binding protein is incorporated into an expression vector and is introduced into *E. coli*, and the *E. coli* is cultured while expression of protein is induced. Conditions for induction, such as an expression vector and host *E. coli* strains, culture medium components, IPTG concentration, and culture temperature, can be appropriately selected.

Addition of Biological Sample to Carrier

A biological sample and a cell homogenate extract can be added to a carrier by any method. The biological sample, however, must come into contact with the cell homogenate extract during or before the contact of the biological sample with the carrier. That is, the biological sample may be put into sufficient contact with the cell homogenate extract, and components derived from the cell homogenate extract are not necessarily added to the carrier finally, together with the biological sample. For example, a carrier to which the cell homogenate extract component is bound may be prepared, and a biological sample may be added thereto, and the treated sample may be used. Specifically, in an embodiment, the biological sample is allowed to pass through a cell homogenate extract component column.

After the addition, the biological sample and the cell homogenate extract are reacted with the carrier, but not limited to, at 10° C. to 30° C., preferably 20° C. to 30° C., for 10 min to 4 hr, preferably 30 min to 2 hr.

4. Method of Detection of Substance to be Detected

The method of detection according to the present invention detects a substance to be detected specifically bound to the biotinylated protein in step 4).

Persons skilled in the art can appropriately select the method for detecting a substance to be detected based on the properties of a desired protein. Preferred examples of such a method include immunoassays such as enzyme-linked immunosorbent assay (ELISA, including sandwich ELISA)) and radioimmunoassay (RIA); and other assays such as nucleic acid hybridization assay and surface plasmon resonance assay. After a sample to be tested is reacted with a substance that specifically binds and interacts with a substance to be detected and that is immobilized by avidin-biotin binding, the substance to be detected is detected.

In the immunoassay for measuring, for example, an antibody, an antigen is immobilized and is allowed to react with the antibody present in a sample to be tested, and the reaction product is detected by any method well known to persons skilled in the art. For example, in the case where the sample to be tested is one derived from human being, the human antibody bound to the antigen is detected using an anti-human antibody. In this procedure, the anti-human antibody is labeled with a fluorescent material, enzyme, or radioisotope, and the fluorescence intensity, enzyme activity, or radiation dose is finally measured to indirectly measure or determine the amount of the antibody. When the substance to be determined is an antigen, an antibody against one site (epitope) of the antigen is immobilized and is allowed to react with the antigen present in a sample to be tested, and an antibody against another epitope of the antigen is further reacted with the antigen. In this procedure, this secondary antibody against the other epitope is labeled as described above to indirectly measure the amount of the antigen. Alternatively, in the nucleic acid hybridization assay, a nucleic acid composed of several tens of nucleotides to several hundreds or several thousands nucleotides and having a sequence region complementary to a nucleic acid to be determined is immobilized through between biotin and a biotin-binding protein. This is reacted with a sample to be tested containing a nucleic acid labeled with a fluorescent material or radioisotope, and the amount of the fluorescence or isotope is measured.

Any labeling well known to persons skilled in the art may be employed. Alternatively, commercially available fluorescence- or enzyme-labeled anti-human antibodies may be used. Examples of the fluorescence labeling include labeling using, for example, fluorescein or rhodamine, and labeling using a fluorescent protein such as a green fluorescent protein (GFP). Enzymes used for enzyme labeling are, but not limited to, peroxidase, alkaline phosphatase, luciferase, and glucose oxidase. Substrates for measurement using these enzymes are commercially available. For example, TBA and substrates for chemiluminescence can be used for peroxidase. Examples of the radioisotope include iodine ($^{125}$I and $^{121}$I) carbon ($^{14}$C), sulfur ($^{35}$S), and tritium ($^{3}$H), and phosphorus ($^{32}$P) for nucleic acids.

The amount of an antigen or an antibody present in the biological sample (specimen) can be readily calculated by comparison with the amount present in a standard preparation (e.g., a standard sample of a healthy subject or a typical patient in the case of clinical samples) using a linear regression computer algorithm. Such assay for detecting an antigen or an antibody, for example, ELISA is disclosed in Iacobelli et al., Breast Cancer Research and Treatment, 11: 19-30 (1988).

For example, in the case that the amount of the substance to be detected, e.g., antibody, in a biological sample is small (the case of a low antibody titer) or that the degree of non-specific binding due to a biological sample, such as serum, per se is large, the effect of background signals due to non-specific binding would be noticeable. Accordingly, the substance to be detected can be more precisely determined by appropriately subtracting the background signals from the measured value. Persons skilled in the art can appropriately determine the background signal to be subtracted depending on each experimental system.

For example, an example of such an embodiment is a "Human/Monkey anti-type I and type II Collagen IgG Antibody assay kit" (manufactured by Chondrex), which detects an antibody against collagen present in serum. In this kit, the background value (measured value of the secondary antibody only without addition of serum) is subtracted from the measured value of a sample.

In the case where the degree of non-specific binding due to a biological sample, such as serum, per se is large, in order to subtract the background due to the non-specific reaction, as described in Example 2, the following embodiment is also effective: The measured value in the section where a biotinylated SITH-1 antigen (protein that specifically binds to the substance to be detected) is not immobilized (however, in the section, tamavidin had been immobilized to the carrier, and blocking with BSA or the like has been operated, and the serum (biological sample) containing the anti-SITH-1 antibody (the substance to be detected in the biological sample) has been added, as in the section where the SITH-1 antigen is immobilized) is subtracted from the measured value at the carrier on which the biotinylated SITH-1 antigen is immobilized through tamavidin.

Preferably, the amount can be more precisely determined by subtracting the measured value in the section where any protein of which antibody is not possessed by an organism (e.g., human being in the case of SITH-1) from which the sample is derived is immobilized (a non-limiting example of the immobilized protein is green fluorescent protein (GFP), for a mammalian organism). The procedure of immobilization is not particularly limited, and, preferably, the protein is biotinylated and is immobilized on a carrier on which a biotin-binding protein is immobilized, through binding between biotin and the biotin-binding protein.

Persons skilled in the art can appropriately design and select the method of calculation as in above based on the properties of a biological sample and the characteristics of an antibody used.

The method of detection according to the present invention can specifically detect an antibody having a low antibody titer in, preferably, serum.

II. Diluent for Biological Sample

The present invention also provides an agent for diluting a biological sample that is used in a system detecting a substance in the biological sample.

The diluent of the present invention includes
1) a cell homogenate extract and a biotin-binding protein, or
2) a cell homogenate extract prepared from cells genetically engineered to express a biotin-binding protein.

This diluent is an agent for diluting a biological sample prior to addition of the biological sample to a carrier on which a biotinylated protein, the biotinylated protein being a protein that specifically binds to a substance to be detected and has been biotinylated, is immobilized through binding between biotin and a biotin-binding protein in a system detecting the substance in a biological sample. The composition of the diluent of the present invention is preferably selected depending on the production processes of the proteins immobilized on the carrier, that is, a biotin-binding protein, a protein that specifically binds to a substance to be detected, and/or a biotinylated protein.

Specifically, in a system for detecting a substance in a biological sample, cells that are the same species as that of host cells used for expressing the biotin-binding protein, the protein that specifically binds to a substance to be detected, and/or the biotinylated protein are preferably used.

The diluent of the present invention may contain 1) a cell homogenate extract and a biotin-binding protein. This can be used in the embodiment of step 3) (b-i) in a method for detecting a substance in a biological sample of the present invention. Alternatively, the diluent may contain 2) a cell homogenate extract prepared from cells genetically engineered to express a biotin-binding protein. This can be used in the embodiment of step 3) (b-ii).

The "agent for diluting a biological sample" may be a cell homogenate extract itself (and biotin-binding protein) or may be an agent for further diluting a cell homogenate extract together with a biological sample and containing a solvent such as a suitable buffer solution, a commercially available cell diluent, or a serum diluent.

III. Kit

The present invention also provides a kit for detecting a substance in a biological sample. The kit of the present invention includes:

A) a carrier on which a biotinylated protein, the biotinylated protein being a protein that specifically binds to a substance to be detected and has been biotinylated, is immobilized through binding between biotin and a biotin-binding protein; and an agent for diluting a biological sample, including B-i) a cell homogenate extract prepared from cells of the same species as that of the host cells used for expressing the biotin-binding protein, the protein that specifically binds to a substance to be detected, and/or the biotinylated protein in step A), and a biotin-binding protein, or B-ii) a cell homogenate extract prepared from cells of the same species as that of the host cells used for expressing the biotin-binding protein, the protein that specifically binds to a substance to be detected, and/or the biotinylated protein in step A) and genetically engineered to express a biotin-binding protein.

The "agent for diluting a biological sample" may be a cell homogenate extract itself (and biotin-binding protein) or may be an agent for further diluting a cell homogenate extract together with a biological sample and containing a solvent such as a suitable buffer solution, commercially available cell diluent, or a serum diluent.

EXAMPLES

The present invention will now be described specifically by way of the following examples, which are not intended to limit the technical scope of the invention. Based on the descriptions in the specification, modifications and changes will be apparent to persons skilled in the art, and such modifications and changes fall within the technical scope of the invention.

In Examples in the specification, a fusion protein between a human herpes virus 6 (HHV-6)-derived SITH-1 protein and a biotinylation sequence (BioEase tag, Invitrogen) was expressed in $E.\ coli$, and an $E.\ coli$ crude extract obtained therefrom was directly reacted with a microplate on which tamavidin 2 (hereinafter referred to as "TM2") is immobilized to bind the fusion protein to the microplate through tamavidin-biotin binding.

The resulting SITH-1 protein-bound plate was reacted with human serum diluted with an $E.\ coli$ crude extract (supplemented with rabbit anti-SITH-1 antibody; in this test, since a commercially available human serum does not contain anti-SITH-1 antibody, serial dilutions of rabbit anti-SITH-1 antibody (antiserum) were added to the commercially available human serum, and the resulting mixtures were used as specimens) to measure the titer of anti-SITH-1 antibody contained in the human serum.

Example 1

Construction of Vector for Expression of Fusion Protein of SITH-1 and Biotinylation Sequence BioEase Tag)

A gene encoding a fusion protein having a BioEase tag located at the N-terminal side of an SITH-1 protein was designed. This BioEase tag is a peptide tag containing a sequence that is biotinylated in vivo (in this case, $E.\ coli$) by a biotinylation enzyme in a living organism. The amino acid sequence of a BioEase-SITH-1 fusion protein is shown in SEQ ID NO: 8, and the nucleotide sequence encoding the protein is shown in SEQ ID NO: 9.

1-1. Design of Primer

In order to construct a BioEase-SITH-1 fusion gene, first, primers for amplifying an SITH-1 gene were designed. That is, a primer (SITH1NtermGW-F) consisting of a DNA sequence encoding the N-terminal region of an SITH-1 protein and a primer (SITH1 CtermGW-R) consisting of a DNA sequence encoding the C-terminal region of the SITH-1 protein in the reverse direction were designed.

The primers for constructing a fusion gene of SITH-1 and BioEase tag are summarized in Table 1.

TABLE 1

Primers for SITH-1 gene application

| Name | Sequence | Length |
|---|---|---|
| SITH1NtermGW-F | GGATATGAAGAAAAAGTGTC (SEQ ID NO: 10) | 20 mer |
| SITH1CtermGW-R | TTACACATTCATTTCAGTTT (SEQ ID NO: 11) | 20 mer |

1-2. PCR

The SITH-1 region was amplified with the primers, SITH1NtermGW-F and SITH1CtermGW-R, using a DNA of an expression vector carrying the SITH-1 gene (ORF) (SEQ ID NO: 2) with the FLAG-tag (PCT/JP2008/67300) as a template. PCR reaction was performed using a GeneAmp PCR System 9600 (PERKIN ELMER) in 20 μL of a reaction solution containing a template DNA (500 ng), 10×ExTaq buffer (2 μL, TaKaRa), 2.5 mM dNTP (1.6 μL), primers (20 pmoles each), and 5 U/μL ExTaq (0.1 μL) under reaction conditions: 96° C. for 3 min. once, (95° C. for 1 min, 60° C. for 1 min., 72° C. for 2 min.)×20 cycles, and 72° C. for 6 min. once. As a result, a PCR product of 477 bp was obtained.

1-3. Cloning

The SITH-1 gene obtained by PCR was cloned into a vector, pCR8/GW/TOPO (Invitrogen). A ligation reaction was performed according to the instruction attached to the vector kit. The DNA was introduced into *E. coli* TB1 by electroporation, and the plasmid DNA was extracted in a routine manner (Sambrook et al., 1989, Molecular Cloning, A laboratory manual, 2nd edition). Each plasmid for which the presence of an insert was confirmed was analyzed with M13 primers (TaKaRa) and an ABI PRISM fluorescent sequencer (Model 310 Genetic Analyzer, Perkin Elmer) to determine its nucleotide sequence, which was then confirmed to have no mutation in comparison with the sequence of the designed gene.

The plasmid carrying the SITH-1 gene was used as an entry clone and subjected to a recombination reaction with pET104.1 destination vector (Invitrogen), an expression vector for a BioEase tag-fused protein, using a Gateway System. The recombinant product was transformed into *E. coli* TB 1 and the plasmid DNA was extracted. This plasmid was further transformed into *E. coli* BL21 (DE3). The resulting *E. coli* colonies were each used as a template to amplify an insert gene region by PCR with SITH1NtermGW-F and SITH1 CtermGW-R to thereby confirm the presence or absence of the insert gene.

In the manner described above, a vector for BioEase tag-fused SITH-1 protein expression, BioEase-SITH1/pET104.1, was completed.

1-4. *E. coli* Expression

*E. coli* BL21 (DE3) carrying BioEase-SITH1/pET104.1 or *E. coli* BL21 carrying pTrc99A alone (as a control) was inoculated into LB medium (50 mL) containing an antibiotic, ampicillin (final concentration: 100 μg/mL) and cultured with shaking at 30° C. until the absorbance at OD600 reached 0.5. Then, 1 mM IPTG was added thereto, and the *E. coli* cells were further cultured with shaking at 30° C. for 5 hr. The cultured solution (50 mL) was centrifuged to collect the cells. The cells were suspended in 3 mL of 0.1 M HEPES/KOH (pH 7.4) and then homogenized by ultrasonication. The homogenate was centrifuged (15,000 rpm), and the resulting supernatant was used as an *E. coli* crude extract.

To confirm the expression of the BioEase tag-fused SITH-1 protein, proteins contained in each crude extracts were fractionated by SDS-PAGE and analyzed by Western blotting. In Western blotting for detection of BioEase tag-fused SITH-1, rabbit anti-SITH-1 antibody (unpublished) and alkaline phosphatase-labeled anti-rabbit IgG antibody (BIO RAD) were used.

The results are shown in FIG. 1A. A band of approximately 30 kDa, which was not found in the control, was detected from the BioEase tag-fused SITH-1-expressing *E. coli*. This size was substantially equal to the molecular weight (28.6 kDa) of BioEase tag-fused SITH-1.

Furthermore, horseradish peroxidase-labeled streptavidin was used in place of anti-SITH-1 antibody to detect signals. The results are shown in FIG. 1B. In the control, almost no signal was detected, whereas two thick bands originating from proteins that react with streptavidin (i.e., appear to be biotinylated) were detected from the BioEase tag-fused SITH-1-expressing *E. coli* crude extract. Among them, the upper band was found to have substantially the same size as the band detected by the former Western blotting. These results indicated that the expression of biotinylated SITH-1 was successful.

In addition to the above extracts, for use in the subsequent ELISA experiment, additional *E. coli* crude extracts were prepared in the same manner from *E. coli* BL21 carrying pTrc99A or TM2/pTrc99A (WO2002/072817) after culturing in the presence of IPTG.

Example 2

Elisa Detection of Anti-SITH-1 Antibody in Human Serum

Purified TM2 was immobilized on a microplate using a New ELISA plate kit (Sumitomo Bakelite Co., Ltd., Japan). Immobilization was accomplished according to the instructions attached to the kit.

The BioEase tag-fused SITH-1 protein-expressing *E. coli* crude extract obtained in Example 1 was adjusted to have a total protein concentration of 2 mg/mL with 0.1 M HEPES/KOH (pH 7.4), 100 μL of which was then added to a TM2-immobilized plate (Sumitomo Bakelite Co., Ltd., Japan, New ELISA). The plate was allowed to stand at room temperature for 1 hr to thereby bind the BioEase tag-fused SITH-1 protein onto the TM2-immobilized plate through tamavidin-biotin binding. Then, each well of the plate was washed with a 0.1% Tween 20-containing TBS buffer solution (TBST) three times, followed by addition of a 5 μg/mL BSA/TBST solution in a volume of 250 μL per well. The plate was allowed to stand at room temperature for 1 hr to block each well. Then, each well was washed with TBST three times.

Then, a human serum (Human Serum pool, manufactured by Cosmo-Bio, Inc.) was diluted 100-fold with PBS or pTrc99A-carrying or TM2/pTrc99A-carrying *E. coli* crude extract (1 mg total soluble protein/mL) prepared in (1-4) of Example 1. To the resulting solution, rabbit anti-SITH-1 antibody was added in serial dilution to give volume ratios of 1/500, 1/1000, 1/2000, 1/4000, and 1/8000. These human serum dilutions (containing anti-SITH-1 antibody) were added in a volume of 100 μL to the plate on which the BioEase tag-fused SITH-1 protein was immobilized through biotin-tamavidin 2 binding, followed by incubation for 1 hr at room temperature.

It is expected that the antibody titer in serum of the rabbit anti-SITH-1 antibody (antiserum) is about 50 times higher compared to the SITH-1 antibody titer in serum of a patient with a typical depression (mood disorder). Accordingly, pseudo sample for serum of a patient with a typical depression can be prepared by mixing 1/50 volume of rabbit anti-SITH-1 antibody (antiserum) to a commercially available human serum (of a healthy person). Accordingly, the dilution rates of the antibody as discussed above provide samples similar to those when serum of depression patients are used after about 10 to 80 folds dilutions.

Furthermore, to confirm the effect of TM2 in the *E. coli* crude extracts used for serum dilution, a solution was prepared to contain purified TM2 at a final concentration of 50 μg/mL in PBS or in the above pTrc99A-carrying *E. coli* crude extract. Human serum was diluted 100-fold with this solution, and to the resulting solution, rabbit anti-SITH-1 antibody was added in serial dilution to give volume ratios of 1/500, 1/1000, 1/2000, 1/4000, and 1/8000, as in the case mentioned above. These dilutions were added in a volume of 100 μL to the plate on which BioEase tag-fused SITH-1 was immobilized, followed by incubation for 1 hr at room temperature. As a control, a TM2-immobilized plate on which nothing was bound was also blocked as described above. Human serum was diluted 100-fold with the same PBS solution or the same pTrc99A-carrying or TM2/pTrc99A-carrying *E. coli* crude extract (1 mg total soluble protein/mL) as used above, or alternatively, with the purified TM2-supplemented PBS or with the purified TM2-supplemented pTrc99A-carrying *E. coli* crude extract, followed by addition of serially diluted rabbit anti-SITH-1 antibody. The resulting dilutions were added in a volume of 100 μL to the control plate and incubated at room temperature for 1 hr.

The thus prepared human serum samples, which were diluted with various diluents and supplemented with serially diluted rabbit anti-SITH-1 antibody, were each reacted with the BioEase tag-fused SITH-1 protein immobilized on the carrier, followed by washing with TBST three times. Then, to detect each of the rabbit anti-SITH-1 antibody bound to SITH-1 and the human IgG in serum which is presumed to be non-specifically bound in each well, a mixture of horseradish peroxidase-labeled goat anti-rabbit IgG antibody and peroxidase-labeled goat anti-human IgG antibody, each of which was diluted 5000-fold with TBST, was added in a volume of 100 μL per well, followed by incubation for 1 hr at room temperature. Then, each well was washed with TBST three times and peroxidase activity was detected. The activity was measured as follows: To each well, SuperSignal ELISA Pico Chemiluminescent Substrate (PIERCE) was added in a volume of 100 μL and allowed to stand for 5 min at room temperature, followed by measuring the luminescence intensity with a plate reader Infinite M200 (TECAN). Note that the data also include a luminescence intensity value measured at each concentration of rabbit anti-SITH-1 antibody for the control section sample (i.e., the region wherein the TM2 plate on which BioEase tag-fused SITH-1 was not immobilized, but which was blocked and treated with human serum containing anti-SITH-1 antibody at each concentration). The value of the control section was subtracted from the luminescence intensity value of each BioEase tag-fused SITH-1-immobilized section. The resulting value was defined as the detected amount of anti-SITH-1 antibody contained in the serum. Further, the S/N ratio was calculated by the equation shown below to compare the effect of each serum dilution.

S/N ratio=Detected amount of anti-SITH-1 antibody in a section containing anti-SITH-1 antibody at each concentration/Detected amount of anti-SITH-1 antibody in a section free from anti-SITH-1 antibody The equation shows that the detection sensitivity is higher when S/N ratio is larger.

The results are shown in FIGS. 2 and 3. The anti-SITH-1 antibody contained in the serum showed non-specific binding in most of the serum sections diluted with PBS, and a high level of luminescence intensity was also detected in the sections free from anti-SITH-1 antibody. Moreover, this problem of non-specific binding was not improved in the presence of 50 μg/mL TM2. In contrast, in the serum sections diluted with the pTrc99A-carrying *E. coli* crude extract or with the TM2/pTrc99A-carrying *E. coli* crude extract or in the serum sections diluted with the pTrc99A-carrying *E. coli* crude extract supplemented with 50 μg/mL TM2, luminescence intensity was significantly low in sections without addition of the SITH-1 antibody to dramatically reduce non-specific binding (FIG. 2).

As shown in FIG. 3, the S/N ratio was particularly high in the sections diluted with the pTrc99A-carrying *E. coli* crude extract supplemented with 50 μg/mL TM2 and in the sections diluted with the TM2/pTrc99A-carrying *E. coli* crude extract.

These results indicated that in the measurement system using a TM2 plate on which BioEase tag-fused SITH-1 was immobilized, dilution of human serum with a TM2-containing *E. coli* crude extract allowed a reduction of non-specific binding originating from the human serum, thereby enabling the sensitive and quantitative detection of anti-SITH-1 antibody even at a very low concentration.

Sequence Listing Free Text
 SEQ ID NO: 1: amino acid sequence of SITH-1
 SEQ ID NO: 2: nucleotide sequence of SITH-1ORF
 SEQ ID NO: 3: nucleotide sequence of SITH-1 cDNA
 SEQ ID NO: 4: nucleotide sequence of tamavidin 1
 SEQ ID NO: 5: amino acid sequence of tamavidin 1
 SEQ ID NO: 6: nucleotide sequence of tamavidin 2
 SEQ ID NO: 7: amino acid sequence of tamavidin 2
 SEQ ID NO: 8: amino acid sequence of BioEase-SITH-1 fusion protein
 SEQ ID NO: 9: nucleotide sequence encoding BioEase-SITH-1 fusion protein
 SEQ ID NO: 10: PCR primer SITH1NtermGW-F
 SEQ ID NO: 11: PCR primer SITH1NtermGW-R

The invention claimed is:

1. A method for detecting a substance in a biological sample, which comprises:
   1) providing a carrier on which a biotin-binding protein is bound and providing a biotinylated protein by biotinylating a protein that specifically binds to a substance to be detected;
   2) immobilizing the biotinylated protein to the carrier provided in step 1) through binding between biotin and the biotin-binding protein to produce a biotinylated protein-bound carrier;
   3) mixing
   (a) a biological sample, and
   (b-i) a cell homogenate extract prepared from cells of the same species as that of the host cells used for expressing the biotin-binding protein, the protein that specifically binds to a substance to be detected, and/or the biotinylated protein in step 1), and a biotin-binding protein, or
   (b-ii) host cells used for expressing the biotin-binding protein, the protein that specifically binds to a substance to be detected, and/or the biotinylated protein in step 1), and the cell genetically engineered to express a biotin-binding protein;
   4) adding the mixture in step 3) to the biotinylated protein-bound carrier produced in step 2); and
   5) detecting a substance specifically bound to the biotinylated protein immobilized onto the carrier.

2. The method according to claim 1, wherein step 3(b-i) in claim 1 comprises adding a cell homogenate extract extracted from cells comprising a vector, as the cell homogenate extract,
   wherein the vector is selected from:
      an empty vector of the same species as that of the vector used in expression of the biotin-binding protein, the protein that specifically binds to a substance to be detected, and/or the biotinylated protein and not containing a gene that encodes these proteins,
      a vector further containing any nucleic acid in the empty vector, or
      an empty vector of the different species as that of the vector used in expression of the biotin-binding protein, the protein that specifically binds to a substance to be detected, and/or the biotinylated protein.

3. The method according to claim 1 or 2, wherein the biotin-binding protein is selected from the group consisting of:
   (1) a protein comprising an amino acid sequence selected from SEQ ID NO:5 or SEQ ID NO:7; and
   (2) a protein comprising an amino acid sequence sharing an identity of 80% or more to an amino acid sequence selected from SEQ ID NO:5 or SEQ ID NO:7.

4. The method according to claim 1, wherein the biological sample is selected from the group consisting of blood, serum, cerebrospinal fluid, saliva, throat swab, sweat, urine, tear, lymph fluid, semen, ascites, and mother's milk.

5. A kit for detecting a substance in a biological sample, which comprises:
   A) biotin-binging protein;
   B) a carrier on which a biotinylated protein, the biotinylated protein being a protein that specifically binds to a substance to be detected and has been biotinylated, is immobilized through binding between biotin and the biotin-binding protein; and
   an agent for diluting a biological sample, comprising
   C-i) a cell homogenate extract prepared from cells of the same species as that of the host cells used for expressing the biotin-binding protein, the protein that specifically binds to a substance to be detected, and/or the biotinylated protein of part A), and a biotin-binding protein, or
   C-ii) a cell homogenate extract prepared from cells of the same species as that of the host cells used for expressing the biotin-binding protein, the protein that specifically binds to a substance to be detected, and/or the biotinylated protein of part A) and genetically engineered to express a biotin-binding, protein.

* * * * *

SEQUENCE LISTING

<160> NUMBER OF SEQ ID NOS: 11

<210> SEQ ID NO 1
<211> LENGTH: 159
<212> TYPE: PRT
<213> ORGANISM: Human herpesvirus 6

<400> SEQUENCE: 1

Met Gly Tyr Glu Glu Lys Val Ser Ala Thr Gly Lys Thr Arg Leu Lys
1               5                   10                  15

```
Ile Leu Ala Cys Leu Ile Val Leu Ile Leu Ala Ala Ala Ile Thr Met
             20                  25                  30

Leu Thr Leu Glu Ile Ile Ser Asn Gln Lys Arg Thr Thr Thr Asp Leu
         35                  40                  45

Glu Ala Val Thr Val Ala Leu Lys His Val Ser Thr Ser Leu Ala Ser
     50                  55                  60

Cys Thr Glu Ser Thr Thr Ser Val His Thr Asp Ser Val Thr Ser Gln
 65                  70                  75                  80

Pro Thr Lys Asn Lys Glu Ser Arg Lys Lys Ile Glu Gly Lys Ser Pro
                 85                  90                  95

Ser Trp Val Gln Ala Leu Thr Thr Ala Ser Gly Ile Ile Leu Leu Phe
                100                 105                 110

Cys Ile Met Met Ile Phe Ile Thr Cys Ser Trp Thr Thr Glu Lys Asp
            115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val
145                 150                 155
```

<210> SEQ ID NO 2
<211> LENGTH: 480
<212> TYPE: DNA
<213> ORGANISM: Human herpesvirus 6

<400> SEQUENCE: 2

```
atgggatatg aagaaaaagt gtcagctact ggaaagactc gtttaaagat actggcatgt     60
ctgatcgttt taatactagc tgcggcaata actatgttaa cgctggaaat tatatcgaac    120
caaaaacgta ccactactga tctcgaagct gtgactgtgg cgctgaagca tgtaagcaca    180
tctcttgcca gctgcactga tccactactc tctgtacata ccgattctgt gacgagccaa    240
cccacgaaaa acaaagaatc gaggaaaaaa attgaaggga atctccaagt tgggttcag    300
gctttaacta cagcatctgg aattatccta ctgttttgta atgatgat   attcattaca    360
tgttcctgga ccacagaaaa agatacagag aagagtgaag tgcaatctta tgcttcttca    420
gtagagactt tagactcttt aaatgaggct attataccga aaactgaaat gaatgtgtaa    480
```

<210> SEQ ID NO 3
<211> LENGTH: 1795
<212> TYPE: DNA
<213> ORGANISM: Human herpesvirus 6

<400> SEQUENCE: 3

```
aggctctgct ggaggctctg ctggaggcct tgctgaaggc tctgctggag gccctgctgg     60
aggtcttgct ggaggctctg ctggaggctc tgctggaggc tctgctggag gctctgctgg    120
aggctctgct ggaggctctg ctggaggctc tgtcagagac ctcggtgaaa gtttactca    180
gaggtttatc agagttttcg ccattagttt ggttagaagt ttcagattta ttttcggtgg    240
aactgcagtt aggtttcatg tcagtacatt catcaccgtt agaagtgcta ttcatggtgc    300
tgttgccact gttggattg  ttaaaagcag taaatgagct aggattggaa tgactccgaa    360
tagctaataa atttgagcat tttcttcgaa tggatcataa tcagagggat agccatctaa    420
tttaaagact tccattttat cactgttgca atcacttcta atggagtatc tggatacatt    480
ttttctcact cttttcatc  ccctccaaca tggatctgtg cagcgttaat aagccagcgg    540
agttaattaa atcgtcttcc atgttagaca gttcctgttt catggcagcc ttcactgatg    600
```

```
caccaatact ttggatgcaa gtgccaacgg actgagctag gatgtaaaag aagatattct    660
aattttgaat tcttcagatg ctccttcttc cacattactg gaataggaca cattcttgga    720
agcgatgtcg ttggaagact ctgggatgaa aagatcacag gcttccagtt ctggaaaaag    780
caggctttca aaggacacat cacacttgag actctcttcc aatatttctt tgatggattc    840
ttccaccact ggatcgggat ggtagctata tatactatat aaggagatta ccaccaccac    900
ctctttcttt gcagagatta ttctctgctt gaaaatctgt aacactgatc atgatgggat    960
atgaagaaaa agtgtcagct actggaaaga ctcgtttaaa gatactggca tgtctgatcg   1020
ttttaatact agctgcggca ataactatgt taacgctgga aattatatcg aaccaaaaac   1080
gtaccactac tgatctcgaa gctgtgactg tggcgctgaa gcatgtaagc acatctcttg   1140
ccagctgcac tgaatccact acttctgtac ataccgattc tgtgacgagc caacccacga   1200
aaaacaaaga atcgaggaaa aaaattgaag ggaaatctcc aagttgggtt caggctttaa   1260
ctacagcatc tggaattatc ctactgtttt gtataatgat gatattcatt acatgtccct   1320
ggaccacaga aaaagataca gagaagagtg aagtgcaatc ttatgctcct tcagtagaga   1380
ctttagaccc tttaaatgag gctattatac cgaaaactga aatgaatgtg taatgtctgt   1440
atttttcttt acagagatgt acggagagtt tatatttggg gaaaatacct gactgttctg   1500
cctatatgcg aatgttaaag tatgtataat ataaattctt accttttaag agtgattcaa   1560
ggtggaggtt tctttggaga ttgattccag gtggtggttt cgggtgcaat caatctttct   1620
tctgggcggg aagaaaatcc agcaatccaa taattgatgg gatgtaatca atgtcacaaa   1680
tctgtaagat taaatgtgaa cagtataaat tctttcgtgc ttatcaaatt acaattatgc   1740
gcatgaaaat atcattaaat tgttttaaac attcttaaaa aaaaaaaaaa aaaaa         1795
```

<210> SEQ ID NO 4
<211> LENGTH: 432
<212> TYPE: DNA
<213> ORGANISM: Pleurotus cornucopiae
<220> FEATURE:
<221> NAME/KEY: CDS
<222> LOCATION: (1)..(432)

<400> SEQUENCE: 4

```
atg aaa gac gtc caa tct ctc ctc acc gga acc tgg tac aat gaa ctc     48
Met Lys Asp Val Gln Ser Leu Leu Thr Gly Thr Trp Tyr Asn Glu Leu
1               5                   10                  15 ggc tca aca atg aat ttg act gca aat aaa gac ggt tcg ctc acc gga     96
Gly Ser Thr Met Asn Leu Thr Ala Asn Lys Asp Gly Ser Leu Thr Gly
            20                  25                  30 acg tac cac tcc aac gtc ggc gag gtt ccc cca act tat cac ctt tct    144
Thr Tyr His Ser Asn Val Gly Glu Val Pro Pro Thr Tyr His Leu Ser
        35                  40                  45 ggc cgg tac aac ctc cag ccc ccc tcg ggt caa ggc gtt act ctg gga    192
Gly Arg Tyr Asn Leu Gln Pro Pro Ser Gly Gln Gly Val Thr Leu Gly
    50                  55                  60 tgg gcg gtg tct ttc gaa aac act agt gcg aat gtt cat tct gtc tca    240
Trp Ala Val Ser Phe Glu Asn Thr Ser Ala Asn Val His Ser Val Ser
65                  70                  75                  80 aca tgg agc ggg cag tac ttc tct gaa ccc gcc gag gtg atc ctc acc    288
Thr Trp Ser Gly Gln Tyr Phe Ser Glu Pro Ala Glu Val Ile Leu Thr
                85                  90                  95 cag tgg ctg ttg tca agg agc tct gag cgc gaa gat ttg tgg cag tcc    336
Gln Trp Leu Leu Ser Arg Ser Ser Glu Arg Glu Asp Leu Trp Gln Ser
            100                 105                 110
```

```
acc cat gtg ggg cat gat gag ttc agc aag aca aag cca acc aag gag      384
Thr His Val Gly His Asp Glu Phe Ser Lys Thr Lys Pro Thr Lys Glu
        115                 120                 125 aag att gcc cag gct caa ctc ctt cgt cgc ggg ttg aag ttc gag tga      432
Lys Ile Ala Gln Ala Gln Leu Leu Arg Arg Gly Leu Lys Phe Glu
    130                 135                 140
```

<210> SEQ ID NO 5
<211> LENGTH: 143
<212> TYPE: PRT
<213> ORGANISM: Pleurotus cornucopiae

<400> SEQUENCE: 5

```
Met Lys Asp Val Gln Ser Leu Leu Thr Gly Thr Trp Tyr Asn Glu Leu
1               5                   10                  15

Gly Ser Thr Met Asn Leu Thr Ala Asn Lys Asp Gly Ser Leu Thr Gly
            20                  25                  30

Thr Tyr His Ser Asn Val Gly Glu Val Pro Pro Thr Tyr His Leu Ser
        35                  40                  45

Gly Arg Tyr Asn Leu Gln Pro Pro Ser Gly Gln Gly Val Thr Leu Gly
    50                  55                  60

Trp Ala Val Ser Phe Glu Asn Thr Ser Ala Asn Val His Ser Val Ser
65                  70                  75                  80

Thr Trp Ser Gly Gln Tyr Phe Ser Glu Pro Ala Glu Val Ile Leu Thr
                85                  90                  95

Gln Trp Leu Leu Ser Arg Ser Ser Glu Arg Glu Asp Leu Trp Gln Ser
            100                 105                 110

Thr His Val Gly His Asp Glu Phe Ser Lys Thr Lys Pro Thr Lys Glu
        115                 120                 125

Lys Ile Ala Gln Ala Gln Leu Leu Arg Arg Gly Leu Lys Phe Glu
    130                 135                 140
```

<210> SEQ ID NO 6
<211> LENGTH: 426
<212> TYPE: DNA
<213> ORGANISM: Pleurotus cornucopiae
<220> FEATURE:
<221> NAME/KEY: CDS
<222> LOCATION: (1)..(426)

<400> SEQUENCE: 6

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct     144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95
```

```
ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
        100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
        130                 135                 140
```

<210> SEQ ID NO 7
<211> LENGTH: 141
<212> TYPE: PRT
<213> ORGANISM: Pleurotus cornucopiae

<400> SEQUENCE: 7

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 8
<211> LENGTH: 271
<212> TYPE: PRT
<213> ORGANISM: Artificial Sequence
<220> FEATURE:
<223> OTHER INFORMATION: Fusion protein BioEase Tag-SITH-1

<400> SEQUENCE: 8

```
Met Ala Ser Met Thr Gly Gly Gln Gln Met Gly Ile Met Gly Ala Gly
1               5                   10                  15

Thr Pro Val Thr Ala Pro Leu Ala Gly Thr Ile Trp Lys Val Leu Ala
            20                  25                  30

Ser Glu Gly Gln Thr Val Ala Ala Gly Glu Val Leu Ile Leu Glu
        35                  40                  45

Ala Met Lys Met Glu Thr Glu Ile Arg Ala Ala Gln Ala Gly Thr Val
    50                  55                  60

Arg Gly Ile Ala Val Lys Ala Gly Asp Ala Val Ala Val Gly Asp Thr
65                  70                  75                  80

Leu Met Thr Leu Ala Gly Ser Gly Ser Asp Leu Tyr Asp Asp Asp Asp
                85                  90                  95

Lys Gly Ile Ile Thr Ser Leu Tyr Lys Lys Ala Gly Ser Glu Phe Ala
            100                 105                 110

Leu Gly Tyr Glu Glu Lys Val Ser Ala Thr Gly Lys Thr Arg Leu Lys
```

```
            115                 120                 125
Ile Leu Ala Cys Leu Ile Val Leu Ile Leu Ala Ala Ile Thr Met
    130                 135                 140

Leu Thr Leu Glu Ile Ile Ser Asn Gln Lys Arg Thr Thr Asp Leu
145                 150                 155                 160

Glu Ala Val Thr Val Ala Leu Lys His Val Ser Thr Ser Leu Ala Ser
                165                 170                 175

Cys Thr Glu Ser Thr Thr Ser Val His Thr Asp Ser Val Thr Ser Gln
                180                 185                 190

Pro Thr Lys Asn Lys Glu Ser Arg Lys Lys Ile Glu Gly Lys Ser Pro
            195                 200                 205

Ser Trp Val Gln Ala Leu Thr Thr Ala Ser Gly Ile Ile Leu Leu Phe
    210                 215                 220

Cys Ile Met Met Ile Phe Ile Thr Cys Ser Trp Thr Thr Glu Lys Asp
225                 230                 235                 240

Thr Glu Lys Ser Glu Val Gln Ser Tyr Ala Ser Ser Val Glu Thr Leu
                245                 250                 255

Asp Ser Leu Asn Glu Ala Ile Ile Pro Lys Thr Glu Met Asn Val
            260                 265                 270

<210> SEQ ID NO 9
<211> LENGTH: 816
<212> TYPE: DNA
<213> ORGANISM: Artificial Sequence
<220> FEATURE:
<223> OTHER INFORMATION: DNA encoding fusion protein BioEase Tag-SITH-1

<400> SEQUENCE: 9
atggctagca tgactggtgg acagcaaatg ggtattatgg gcgccggcac cccggtgacc      60
gccccgctgg cgggcactat ctggaaggtg ctggccagcg aaggccagac ggtggccgca     120
ggcgaggtgc tgctgattct ggaagccatg aagatggaaa ccgaaatccg cgccgcgcag     180
gccgggaccg tgcgcggtat cgcggtgaaa gccggcgacg cggtggcggt cggcgacacc     240
ctgatgaccc tggcgggctc tggatccgat ctgtacgacg atgacgataa gggaattatc     300
acaagtttgt acaaaaaagc aggctccgaa ttcgcccttg atatgaaga aaaagtgtca     360 gctactggaa agactcgttt aaagatactg gcatgtctga tcgtttttaat actagctgcg     420 gcaataacta tgttaacgct ggaaattata tcgaaccaaa aacgtaccac tactgatctc     480
gaagctgtga ctgtggcgct gaagcatgta agcacatctc ttgccagctg cactgaatcc     540
actacttctg tacataccga ttctgtgacg agccaaccca cgaaaaacaa agaatcgagg     600
aaaaaaattg aagggaaatc tccaagttgg gttcaggctt aactacagc atctggaatt     660 atcctactgt tttgtataat gatgatattc attcatgtt cctggaccac agaaaaagat     720
acagagaaga gtgaagtgca atcttatgct tcttcagtag agactttaga ctctttaaat     780
gaggctatta taccgaaaac tgaaatgaat gtgtaa                               816

<210> SEQ ID NO 10
<211> LENGTH: 20
<212> TYPE: DNA
<213> ORGANISM: Artificial Sequence
<220> FEATURE:
<223> OTHER INFORMATION: Synthetic primer SITH1NtermGW-F

<400> SEQUENCE: 10
ggatatgaag aaaaagtgtc                                                  20
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic primer SITH1CtermGW-R

<400> SEQUENCE: 11
ttacacattc atttcagttt                                              20
```